US007642048B2

(12) United States Patent
Gabrin et al.

(10) Patent No.: US 7,642,048 B2
(45) Date of Patent: Jan. 5, 2010

(54) CHEMO-SENSITIVITY ASSAYS USING TUMOR CELLS EXHIBITING PERSISTENT PHENOTYPIC CHARACTERISTICS

(75) Inventors: Michael Gabrin, Pittsburgh, PA (US); Stacey Brower, Pittsburgh, PA (US); Sean McDonald, Pittsburgh, PA (US); Holly Gallion, Pittsburgh, PA (US); Payal Nanavati, Pittsburgh, PA (US); Shara Dawn Rice, Pittsburgh, PA (US); Anuja Chattopadhyay, Pittsburgh, PA (US)

(73) Assignee: Precision Therapeutics Inc., Pittsburgh, PA (US)

( * ) Notice: Subject to any disclaimer, the term of this patent is extended or adjusted under 35 U.S.C. 154(b) by 77 days.

(21) Appl. No.: 11/785,984

(22) Filed: Apr. 23, 2007

(65) Prior Publication Data
US 2008/0085519 A1    Apr. 10, 2008

Related U.S. Application Data

(63) Continuation of application No. 11/514,172, filed on Sep. 1, 2006, now abandoned.

(60) Provisional application No. 60/712,815, filed on Sep. 1, 2005, provisional application No. 60/712,814, filed on Sep. 1, 2005, provisional application No. 60/735,813, filed on Nov. 14, 2005.

(51) Int. Cl.
C12N 5/02 (2006.01)
C12N 5/06 (2006.01)
C12Q 1/00 (2006.01)
C12N 5/08 (2006.01)

(52) U.S. Cl. .................. 435/4; 435/374; 435/375; 435/378; 435/379; 435/381

(58) Field of Classification Search ....................... None
See application file for complete search history.

(56) References Cited

U.S. PATENT DOCUMENTS

| | | | |
|---|---|---|---|
| 4,423,145 A | 12/1983 | Stampfer et al. | |
| 4,559,299 A | 12/1985 | Rotman | |
| 4,668,618 A | 5/1987 | Thornthwaite | |
| 4,816,395 A | 3/1989 | Hancock et al. | |
| 4,937,187 A | 6/1990 | Rotman | |
| 4,996,145 A | 2/1991 | Weisenthal | |
| 5,242,806 A | 9/1993 | Yen-Maguire et al. | |
| 5,270,172 A | 12/1993 | Morgan | |
| 5,319,073 A * | 6/1994 | Wank .................. 530/412 | |
| 5,403,574 A | 4/1995 | Piwnica-Worms | |
| 5,443,950 A | 8/1995 | Naughton et al. | |
| 5,607,918 A | 3/1997 | Eriksson et al. | |
| 5,705,270 A | 1/1998 | Soon-Shiong et al. | |
| 5,728,541 A | 3/1998 | Kornblith | |
| 5,789,158 A | 8/1998 | Knowles et al. | |
| 5,874,218 A | 2/1999 | Drolet et al. | |
| 5,888,765 A | 3/1999 | Patterson et al. | |
| 5,942,385 A | 8/1999 | Hirth | |
| 5,972,639 A | 10/1999 | Parandoosh | |
| 6,008,007 A | 12/1999 | Fruehauf et al. | |
| 6,020,473 A | 2/2000 | Keyt et al. | |
| 6,069,134 A | 5/2000 | Roth et al. | |
| 6,111,092 A | 8/2000 | Williamson | |
| 6,261,795 B1 | 7/2001 | Fruehauf et al. | |
| 6,274,576 B1 | 8/2001 | Grimley et al. | |
| 6,303,324 B1 | 10/2001 | Fruehauf | |
| 6,335,170 B1 | 1/2002 | Orntoft | |
| 6,416,967 B2 | 7/2002 | Kornblith | |
| 6,511,806 B1 | 1/2003 | Fruehauf et al. | |
| 6,582,899 B1 * | 6/2003 | Kamb et al. ................ 435/4 | |
| 6,664,062 B1 | 12/2003 | Stanton, Jr. | |
| 6,887,680 B2 | 5/2005 | Kornblith | |
| 6,900,027 B1 | 5/2005 | Kornblith | |
| 6,933,129 B1 | 8/2005 | Kornblith | |
| 7,112,415 B2 | 9/2006 | Kornblith | |
| 7,314,731 B2 | 1/2008 | Kornblith | |
| 7,314,733 B2 | 1/2008 | Conrad et al. | |
| 2001/0051353 A1 | 12/2001 | Kornblith | |
| 2002/0168679 A1 | 11/2002 | Naus et al. | |
| 2002/0192638 A1 | 12/2002 | Kornblith | |

(Continued)

FOREIGN PATENT DOCUMENTS

WO     WO 96/10742     4/1996

(Continued)

OTHER PUBLICATIONS

Hesketh, The Oncogene Handbook, pp. 383 and 457.*

(Continued)

Primary Examiner—Karen A Canella
(74) Attorney, Agent, or Firm—Cooley Godward Kronish LLP

(57) ABSTRACT

The assays, methods, tools and systems discussed herein represent an improved and unified system for monitoring the progression of an individual patient malignancy. The assays, methods, tools and systems discussed herein represent an improved and unified system for monitoring and for identifying cellular and secreted markers, for screening cells to detect phenotypic and genotypic drift and for predicting chemotherapeutic response of patient tumor cells to at least one therapeutic agent. The assays, methods, tools and systems discussed herein also represent an improved and unified system for monitoring and for screening multiple pharmaceutical agents for efficacy and long term effect as to a specific patient.

21 Claims, 4 Drawing Sheets

U.S. PATENT DOCUMENTS

| | | |
|---|---|---|
| 2003/0096290 A1 | 5/2003 | Fruehauf et al. |
| 2004/0023375 A1 | 2/2004 | Kornblith et al. |
| 2004/0072722 A1 | 4/2004 | Kornblith et al. |
| 2004/0086888 A1 | 5/2004 | Kornblith et al. |
| 2005/0202410 A1 | 9/2005 | Kornblith |
| 2007/0037136 A1 | 2/2007 | Kornblith |
| 2007/0059821 A1 | 3/2007 | Kornblith et al. |
| 2007/0082347 A1* | 4/2007 | Lanchbury et al. ............. 435/6 |

FOREIGN PATENT DOCUMENTS

| | | |
|---|---|---|
| WO | WO 98/02038 | 1/1998 |
| WO | WO 02/33117 | 4/2002 |
| WO | WO 2004/015065 | 2/2004 |
| WO | WO 2004/035833 | 4/2004 |

OTHER PUBLICATIONS

Abstract of Neri et al, Nature Biotechnology, 1997, vol. 15, pp. 1271-1275.*
Meyer et al, Current Pharmaceutical Designs, 2006, vol. 12, pp. 2723-2747.*
Kornblith et al (Anticancer Research, 2003, vol. 23, pp. 3405-3412).*
Freshney (The Culture of Animal Cells, 1994, p. 11).*
Hackett et al., Human malignant mammary epithelial cell in culture, in Vitro Models for Cancer Research, vol. 3, pp. 31-49, (1986).
Trent, Functional and morphologic characterization of normal and carcinomatous endometrium in vitro, In Vitro Models for Cancer Research, vol. 3, pp. 153-187, (1986).
Ochs et al., Phenotypic cell culture assay for predicting anticancer drug responses, Preclinica, 2(3), pp. 205-212, (May-Jun. 2004).
Ochs et al., Evidence for the isolation, growth, and characterization of malignant cells in primary cultures of human tumors, In Vitro Cellular and Developmental Biology-Animal, vol. 39, pp. 63-70, (Jan.-Feb. 2003).
Freshney, Culture of animal cells, Other Enzymatic Procedures, p. 142, (1994).
International Search Report based on International Application No. PCT/US2006/034469, (Apr. 15, 2008).
Alley, M., "Morphometric and Colorimetric Analysis of Human Tumor Cell Line Growth and Drug Sensitivity in Soft Agar Culture," Cancer Research, 51:1247-1256 (1991).
Andreotti, P., "TCA-100 Tumour Chemosensitivity Assay: Differences in Sensitivity between Cultured Tumour Cell Lines and Clinical Studies," J. Biolumin. Chemilumin., 9:373-378 (1994).
Arnold, J., et al., "Evaluation of Chemopreventive Agents in Different Mechanistic Classes Using a Rat Tracheal Epithelial Cell Culture Transformation Assay," Cancer Research, 55:537-543 (1995).
Becton-Dickinson Catalog, Anti-Cytokeratin (CAM 5.2) Reagent, pp. 1-11 (1997).
Boehringer Mannheim Catalog, Anti-Cytokeratin AE1/AE3 (1996).
Bosanquet, Andrew G., "Short-term In Vitro Drug Sensitivity Tests for Cancer Chemotherapy. A Summary of Correlations of Test result with Both Patient Response and Survival", Forum 4(2):179-195 (1994).
Broadley, C., et al., "A Tissue-Culture Model for the Study of Canine Vocal Fold Fibroblasts," Laryngoscope, 105(1):23-27 (1995).
Burczynski, M., et al., "Toxicogenomics-Based Discimination of Toxic Mechanism in HepG2 Human Hepatoma Cells," Toxicological Sciences, 58(2):399-415 (2000).
Cilley, R., et al., "Fetal Lung Development: Airway Pressure Enhances the Expression of Developmental Genes," Journal of Pediatric Surgery, 35(1):113-119 (2000).
Dako Catalog, Specification Sheet for Monoclonal Mouse Anti-Human Epithelial Membrane Antigen, pp. 1-2 (1996).
Dietel, M., et al., "In Vitro Prediction of Cytostatic Drug Resistance in Primary Cell Cultures of Solid Malignant Tumours," Eur. J. Cancer, 29A(3):416-420 (1993), Feb. 17, 2009.
Dudley, D., et al.," A Human Endometrial Explant System: Validation and Potential Applications," Am. J. Obstet. Gynecol., 167(6):1774-1780 (1992).
European Search Report for EP 97 93 3267 dated May 3, 2002.

Freshney, R.I., Culture of Animal Cells, 3rd edition, Wiley-Liss, pp. 127-147, 153-156, and 349-356 (1994).
Freshney, R.I., Culture of Animal Cells: A Manual of Basic Technique, 2nd edition, pp. 107, 124-126, 179, 233-234, 290 (1987).
Fruehauf, J.P. "In Vitro Assay-Assisted Treatment selection for Women with Breast or Ovarian Cancer", Endocrine-Related Cancer, 9:171-182 (2002).
Frykholm, G., et al.,"Heterogeneity in Antigenic Expression and Radiosensitivity in Human Colon Carcinoma Cell Lines," In Vitro Cell Dev. Biol., 27A:900-906 (1991).
Fulda, S., et al., "Antiproliferative Potential ofCytostatic Drugs on Neuroblastoma Cells In Vitro," Eur. J. of Cancer., 31A(4):616-621 (1995).
Gamboa, G., et al., "Characterization and Development of UCI 107, a Primary Human Ovarian Carcinoma Cell Line," Gynecologic Oncology, 58:336-343 (1995).
Gerweck, et al., "Radiation Sensitivity of Cultured Human Glioblastoma Cells," Radiology, 125(1):231-234 (1977).
Ghosh, A., et al., "Immunohistological Staining of Reactive Mesothelium, Mesothelloma and Lung Carcinoma with a Panel of Monoclonal Antibodies," J. Clin. Pathol., 40:19-25 (1987).
Goldsworthy, T., et al., "Concepts, Labeling Procedures, and Design of Cell Proliferation Studies Relating to Carcinogenesis," Environmental Health Perspectives, 101(supp. 5):59-65 (1993).
Gress, T., et al.,"Development of a Database on Transcribed Sequences in Tumour Cells and Identification of Changes in Transcription Patterns Related to Transformation and Other Tumour Cell Properties for the Global Finger Printing Analysis of Human Pancreatic Carcinoma cDNA Libraries," Biomedl. Health Res., 24:171-181 (1998).
Guo et al., "Direct flourescence analysis of genetic polymorphisms by hybridization with oligonucleotide arrays on glass supports," Nucleic Acids Research, 22(24):5456-5465 (1994).
Hoffman, R., "The Three-Dimensional Question: Can Clinically Relevant Tumor Drug Resistance be Measured In Vitro?" Cancer and Metastasis Reviews, 13(2):169-173 (1994).
International Search Report for PCT/US01/32540 dated Apr. 18, 2002.
International Search Report for PCT/US97/11595 dated Aug. 17, 1998.
Kaaijk, P., et al., "Daunorubicin and Doxorubicin but not BCNU have Deleterious Effects on Organotypic Multicellular Spheroids of Gliomas," British J. of Cancer, 74(2):187-193 (1996).
Kitamura, M., et al., "Chemosensitivity of Gastric Cancer Using Adhesive Tumor Cell Culture System," Oncology Reports, 2(1):27-31 (1995).
Kornblith, P., "Role of Tissue Culture in Prediction of Malignancy," Clinical Neurosurgery, 25:346-376 (1978).
Kornblith, P., et al., "Variations in Response of Human Brain Tumors to BCNU In Vitro," Journal of Neurosurgery, 48(4):580-586 (1978).
Kruczynski, A., et al., "Evidence of a Direct Relationship Between the Increase in the In Vitro Passage Number of Human Non-Small-Cell-Lung Cancer Primocultures and their Chemosensitivity," Anticancer Research, 13:507-514 (1993).
McGuire, William L. et al., "In Vitro Assays to Predict Drug Sensitivity and Drug Resistance", Breast Cancer Research and Treatment, 12:7-21 (1988).
Nance, K., et al., "Immunocytochemical Panel for the Identification of Malignant Cells in Serous Effusions," Am. J. Clin. Pathol., 95:867-874 (1991).
Persons, D., et al., "Interphase Molecular Cytogenetic Analysis of Epitielial Ovarian Carcinomas," American Journal of Pathology, 142(3):733-741 (1993).
Pfost et al., "A SNPshot: pharmacogenetics and the future of drug therapy," TIBTECH 18:334-338 (Aug. 2000).
Pinkus, G., et al., "Optimal Immunoreactivity of Keratin Proteins in Formalin-Fixed, Paraffin-Embedded Tissue Requires Preliminary Trypsinization," Journal of Histochemistry and Cytochemistry, 33(5):465-473 (1985).
Raju, G., "The Histological and Immunohistochemical Evidence of Squamous Metaplasia from the Myoepithelial Cells in the Breast," Histopathology, 17(3):272-275 (1990).

Raju, G., "Papillary neoplasia of the breast: immunohistochemically defined myoepithelial cells in the diagnosis of benign and malignant papillary breast neoplasms," Mod. Pathol. 2:569-576 (1990).

Robert, J., "Chemosensitivity Testing-Prediction of Response to Anticancer Drugs Using In Vitro Assays", Electronic Journal of Oncology, 2:198-210 (1999).

Singh, H., et al.,"Significance of Epithelial Membrane Antigen in the Work-Up of Problematic Serous Effusions," Diagnostic Cytopathology, 13(1):3-7 (1995).

Stephens, J.C., "Single-nucleotide Polymorphisms, Haplotypes, and Their Relevance to Pharmacogenetics," Molecular Diagnosis 4(4):309-317 (1999).

Stephens, S., et al., "A Longitudinal Study of γ-Interferon Production by Peripheral Blood Mononuclear Cells from Breast- and Bottle-Fed Infants," Clin. Exp. Immunol., 65:396-400 (1986).

Stewart, R., et al., "Glutamate Accumulation By Human Gliomas and Meningiomas in Tissue Culture," Brain Research, 118(3):441-452 (1976).

Stoop, J., et al., "Identification of Malignant Cells in Serous Effusions Using a Panel of Monoclonal Antibodies Ber-EP4, MCA-b-12 and EMA," Cytopathology, 3:297-302 (1992).

Tannock et al., The Basic Science of Oncology, 2nd edition, pp. 247-248, 261-265, 303-306(1992).

Wiseman, I., "A Modification of Hepatest, using the Terasaki Plate, for the Detection of HbsAg in Blood Donors," J. Clin. Pathol., 29(3):264-266 (1976).

Zwergel et al., "A New Serial Transfer Explant Cell Culture System for Human Prostatic Cancer Tissues Preventing Selection Toward Diploid Cells," Cancer Genet. Cytogenet., 101:16-23 (1998).

Koechli, "Chemosensitivity Testing in Gynecologic Malignancies," Klinisches Labor 41(4):241-312 (1995).

PL Kornblith et al., "Response variablility of human brain tumors to AZQ in tissue culture," Journal of Neuro-Onocology, 1986, pp. 49-54, vol. 4, Martinus Nijhoff Publishers, Boston.

RS Weinstein et al., "Ultrastructure of a cloned astrocytoma in tissue culture," Cancer, 1971, pp. 1174-1181, vol. 27.

PMcL Black et al., "Ultrastructural and electrophysiological features of meningioma whorls in tissue culture," Acta Neuropathol (Berl), 1979, vol. 46, pp. 33-38.

RM Scott et al., "Invasiveness in tissue culture: A technique for study of gliomas," Surg Forum, 1978, pp. 531-533, vol. 29.

T. Liszczak et al., "Morphological, biochemical, ultrastructural, tissue culture and clinical observations of typical and aggressive craniopharyngiomas," Acta Neuropathol (Berl), 1978, pp. 191-203, vol. 43.

PL Kornblith et al., "Growth-inhibitory effects of diphenylhydantoin on human brain tumor cells in culture," Neurosurgery, 1978, pp. 122-127, vol. 2.

RR Weichselbaum et al., "Characterization and radiobiologic parameters of medulloblastoma in vitro," Cancer, 1977, pp. 1087-1096, vol. 40.

RL Martuza et al., "Characteristics of human optic gliomas in tissue culture," J. Neurosurg, 1977, pp. 78-84, vol. 46.

MA Oberc-Greenwood, et al., "Ultrastructural features of the lymphocyte-stimulated halos produced by human glioma-derived cells in vitro," Journal of Neuro-Oncology, 1986, pp. 387-396, vol. 3.

BH Smith et al., "Membrane and cytoplasmic changes in 1,3-bis (2-chloroethy 1)- 1 -nitrosourea (BCNU)-sensitive and resistant human malignant glioma-derived cell lines," Journal of Neuro-Oncology, 1983, pp. 237-248, vol. 1.

GA Curt et al., "Phase II and pharmacokinetic study of aziridinyl-benzoquinone (2,5-diaziridinyl-3, 6- bis(carboethoxyamino)-1,4 benzoquinone, diaziquone, NSC 182986) in high grade gliomas," Cancer Research, 1983, pp. 6102-6105, vol. 43, Issue 12 pt 1.

N Shitara et al., "Flowcytometric and cytogenetic analysis of human cultured cell lines derived from high- and low-grade astrocytomas," Acta Neuropathol (Berl), 1983, pp. 40-48, vol. 60.

MK Gumerlock et al., "Chemical differentiation of cultured human glioma cells: Morphologic and immunologic effects," Surgical Forum, 1981, pp. 475-477, vol. XXXII.

PL Kornblith et al., "Growth-inhibitory effect of diphenylhydantoin on murine astrocytomas," Neurosurgery, 1979, pp. 259-263, vol. 5.

MC Trachtenberg et al., "Biophysical properties of cultured human glial cells," Brain Research, 1972, pp. 279-298, vol. 38.

J. Lightbody et al., "Biochemically differentiated clonal human glial cells in tissue culture," J. Neurobiology, 1970, pp. 411-417, vol. 1, No. 4.

PMcL Black et al., "Biophysical properties of human astrocytic brain tumor cells in cell nature," Journal of Cellular Physiology, 1980, pp. 565-570, vol. 105.

TM Liszczak et al., "Ultrastructure of human endometrial epithelium in monolayer culture with and without steroid hormones," in Vitro, 1977, pp. 344-356, vol. 13, No. 6.

TM Liszczak et al., "Procedure for the embedment and ultrastructural visualization of cells cultured on plastic microtest plates," Journal of Immunological Methods, 1977, pp. 131-134, vol. 15.

RM Stewart et al., "Glutamate accumulation by human gliomas and meningiomas in tissue culture," Brain Research, 1976, pp. 441-452, vol. 118.

PL Kornblith et al., "The future of therapy for glioblastoma," Surg Neurol, 1993, pp. 538-543, vol. 39.

PL Kornblith, "Management of malignant gliomas," Neurosurgery Quarterly, 1991, pp. 97-110, vol. 1, Issue 2.

PL Kornblith et al., "Chemotherapy for malignant gliomas," Journal of Neurosurgery, 1988, pp. 1-17, vol. 68, Issue 1.

PE McKeever et al., "Products of cells cultured from gliomas: VI. Immunofluorescent, morphometric, and ultrastructural characterization of two different cell types growing from explants of human gliomas," American Journal of Pathology, 1987, pp. 358-372, vol. 127, Issue 2.

PMcL Black et al., "Immunological, biological, ultrastructural, and electrophysiological characteristics of a human glioblastoma-derived cell culture line," J. Neurosurg., 1982, pp. 62-72, vol. 56.

PL Kornblith, "The role of cytotoxic chemotherapy in the treatment of malignant brain tumors," Surg Neurol, 1995, pp. 551-552, vol. 44.

WC Welch et al., "Morphologic immunologic, biochemical and cytogenetic characteristics of the human glioblastoma-derived cell line, SNB-19," Journal of the Society for In Vitro Biology, 1995, pp. 610-616, vol. 31.

E Sariban et al., "DNA crosslinking responses of human malignant glioma cell strains to chloroethylnitrosoureas, cisplatin and diaziquone," Cancer Research, 1987, pp. 3988-3394, vol. 47, Issue 15.

* cited by examiner

CHEMO-SENSITIVITY ASSAYS USING TUMOR CELLS EXHIBITING PERSISTENT PHENOTYPIC CHARACTERISTICS

RELATED APPLICATIONS

This application is a Continuation of U.S. application Ser. No. 11/514,172, filed Sep. 1, 2006, now abandoned which claims the benefit of U.S. Provisional Application 60/712,815, filed Sep. 1, 2005; U.S. Provisional Application 60/712,814, filed Sep. 1, 2005; and U.S. Provisional Application 60/735,813, filed Nov. 14, 2005, all of which are incorporated by reference in their entirety.

This application is related to but does not claim the benefit of U.S. application Ser. No. 08/679,056, filed Jul. 12, 1996, now U.S. Pat. No. 5,728,541; PCT Application PCT/US97/11595, filed Jul. 10, 1997; U.S. application Ser. No. 09/040,161, filed Mar. 17, 1998, now U.S. Pat. No. 6,900,027; U.S. application Ser. No. 10/205,887, filed Jul. 26, 2002, now U.S. Pat. No. 6,887,680; U.S. application Ser. No. 11/081,827, filed Mar. 17, 2005; U.S. application Ser. No. 09/039,957, filed Mar. 16, 1998, now U.S. Pat. No. 6,933,129; U.S. application Ser. No. 11/073,931, filed Mar. 8, 2005; U.S. application Ser. No. 11/504,098, filed Aug. 16, 2006; Ser. No. 09/189,310, filed Nov. 10, 1998, now U.S. Pat. No. 6,416,967; U.S. application Ser. No. 10/399,563, filed Oct. 18, 2001; PCT Application PCT/US01/32540, filed Oct. 18, 2001; U.S. application Ser. No. 10/208,480, filed Jul. 30, 2002; PCT Application PCT/US03/23888, filed Jul. 30, 2003; U.S. Provisional Application 60/417,439, filed Oct. 10, 2002; U.S. application Ser. No. 10/336,659 filed Jan. 2, 2003; PCT Application PCT/US03/32285, filed Oct. 10, 2003; and U.S. Provisional Application No. 60/819,631, filed Jul. 11, 2006, all of which are herein incorporated by reference in their entirety.

FIELD OF INVENTION

The present invention relates to methods of preparing a tumor cell sample for use in an assay before substantial phenotypic drift of the tumor cell population occurs. In one embodiment of the invention, a cell culture monolayer is formed from a tissue explant treated with collagenase and DNase. In another embodiment, the cell culture is formed from a tissue explant that has been mechanically agitated. The methods of the invention can be used in conjunction with chemosensitivity and chemoresistance assays.

BACKGROUND

In spite of the progress made against cancer, it is still the second-leading cause of death in America after cardiovascular diseases. One of the major hurdles in the battle against cancer is that chemotherapy agent selections for any individual patient are not truly personalized. While "cancers" share many characteristics in common, each particular cancer has its own specific characteristics. Genetics and environmental factors have a complex interplay in severity and prognosis of treatment.

It has been recognized that when patient cells are removed from their in situ locations in tissues and cultured in vitro, the cells are subject to phenotypic and genotypic drift, i.e., they begin to lose some of the morphological features (and components) of some characteristic of their tissue or organ of origin, sometimes as a result of changes in expression of a gene, or expression of mutated gene. As a result, simply excising cells from normal and tumor tissues and culturing them in vitro is not satisfactory, since adaptation to culture conditions causes repression of components that are expressed in tumor tissue or in normal tissue and may also cause expression of components that are not normally present in tumor or normal tissue.

Currently, chemotherapy choices are based primarily on a combination of the average population response, as published in peer reviewed journal articles, and the treating physician's professional experience. In treating cancer patients with highly toxic chemotherapy, oncologists are faced with the challenge of selecting a therapy regimen for a particular patient with prospective indicators as to what drug might actually work best for that specific patient.

Culture condition variations, selective overgrowth of some cells in the population, and genetic variation of in vitro cultured cells may result in inaccurate and unreliable prospective information regarding therapeutic treatments. Physicians need a reliable method of obtaining prospective information to assist in personalizing the therapy based on a patient's in vitro tumor behavior.

SUMMARY OF THE INVENTION

The present invention discloses methods of preparing a tumor cell sample comprising agitating a tumor explant to substantially release tumor cells from the tumor explant, culturing a cell culture monolayer from the released cells and forming a cell suspension from the monolayer before substantial phenotypic drift occurs. In one embodiment, the cell suspension is about 4,000 to 12,000 cells/ml. In one embodiment, the cell suspension is about 4,000 to 9,000 cells/ml. In another embodiment, the cell suspension is about 7,000 to 9,000 cells/ml.

The tumor explant can optionally be treated with collagenase and DNase prior to culturing of a cell culture monolayer. For instance, the Inventors of the present invention have found that ovarian and colorectal tumor explants culture favorably when treated with a Collagenase II and DNase cocktail. In one embodiment, the tumor explant is treated with a cocktail comprising about 0.010% to about 0.60% Collagenase II and about 0.0007% to about 0.005% DNase. In another embodiment, the tumor explant is treated with a cocktail comprising about 0.25% Collagenase II and about 0.001% DNase. In yet another embodiment, the tumor explant is treated with a cocktail comprising about 0.025% Collagenase II and about 0.001% DNase.

Cells from the cell suspension can be inoculated into at least one segregated site. The segregated site can comprise about 100 to 10,000 cells. Each segregated site can comprise, for instance, about 100 to 5,000 cells, about 100 to 2,500 cells, about 100 to 1,000 cells, about 200 to 1,000 cells or about 200 to 500 cells.

Cells from the cell suspension or at a segregated site can be contacted with one or more pharmaceutical agents such as one or more chemotherapeutic drugs or biological agents. In one embodiment, cells are incubated in one or more segregated sites prior to be contacted with a pharmaceutical agent. For instance, cells can be incubated about 4 to about 30 hours prior to contact with an agent. Cells can also optionally be analyzed, for instance, counted, prior to contact with a pharmaceutical agent. In one embodiment, cells are counted after incubation for about 24 hours prior to contact with an agent.

In one embodiment, cells are kept in contact with one or more pharmaceutical agents for 25 to 200 hours. The time a pharmaceutical agent is kept in contact with a cell population can vary based on factors, including, but not limited to, the identity of the pharmaceutical agent. At the end of the period of contact, cells can be counted. In one embodiment, a dose response curve is generated. In another embodiment, a Cytotoxicity Index or normalized Cytotoxicity Index is calculated.

The assays, methods, tools and systems included in the invention disclosed herein address the challenge presented by patients who will undergo initial chemotherapy, have typically failed earlier chemotherapy, and/or have built up drug resistance through multiple lines or courses of chemotherapy, i.e., the most resistant cancer has survived, and become chemoresistant. The assays, methods, tools and systems included in the invention disclosed herein provide prospective information that will assist the oncologist in personalizing the therapy based on the individual's in vitro tumor behavior.

DETAILED DESCRIPTION

Figure 1:
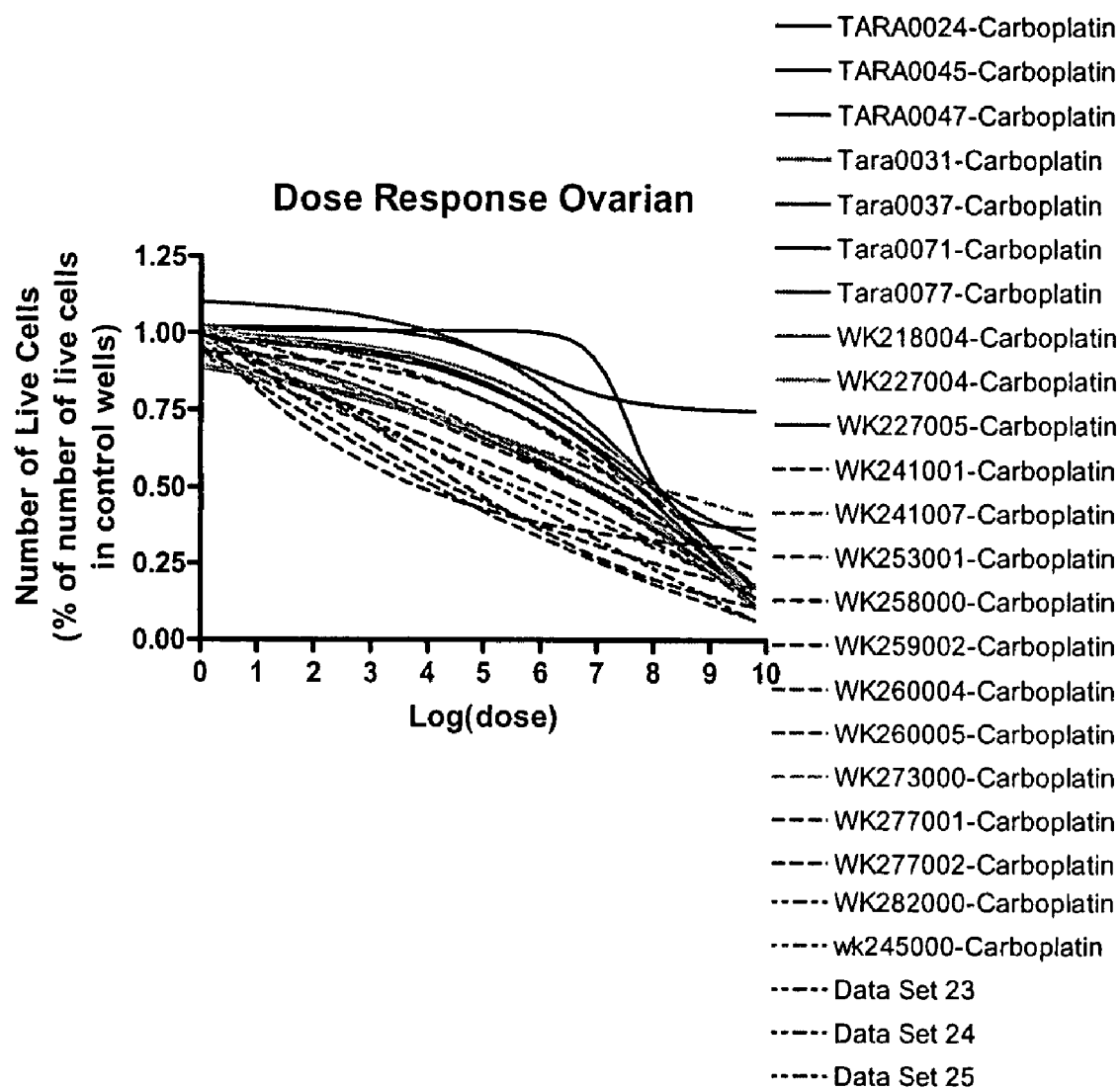
FIG. 1. Representative population distribution achieved during dose setting for carboplatin on ovarian tumor. Specimens are processed and cultured as described in the text. Wells of the microtiter plate are treated with decreasing concentrations from dose 10 to dose 1. Dose 0 is an untreated control well. Fraction cells surviving is determined by averaging three replicate wells at each dose divided by the average of the control well replicates. Each specimen is indicated by a different color line. Lines are non-linear curve fits of raw data.
Figure 2:
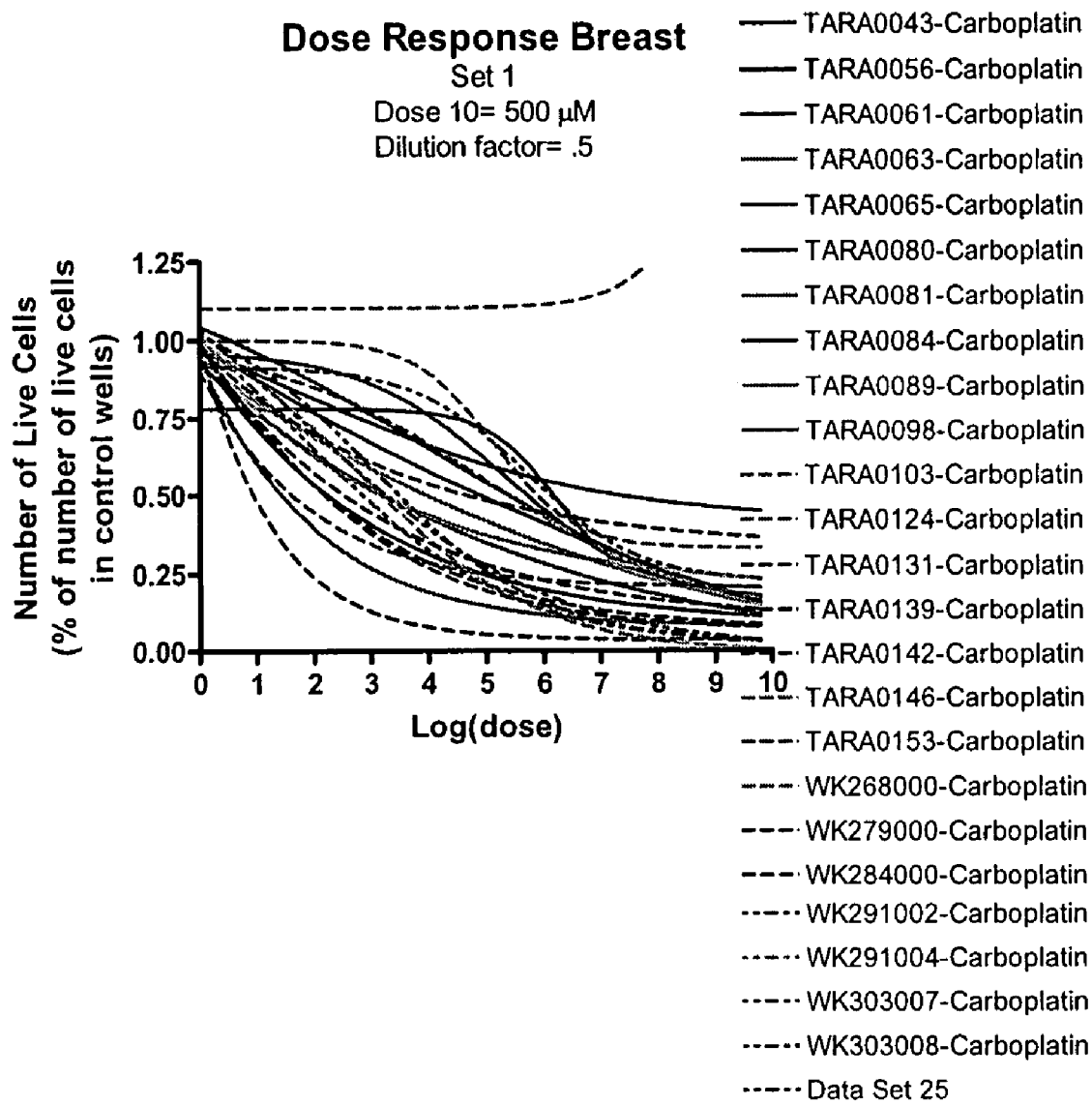
FIG. 2. Representative population distribution achieved during dose setting for Carboplatin on Breast tumor. Specimens are processed and cultured as described in the text. Wells of the microtiter plate are treated with decreasing concentrations from dose 10 to dose 1. Dose 0 is an untreated control well. Fraction cells surviving is determined by averaging three replicate wells at each dose divided by the average of the control well replicates. Each specimen is indicated by a different color line. Lines are non-linear curve fits of raw data.
Figure 3:
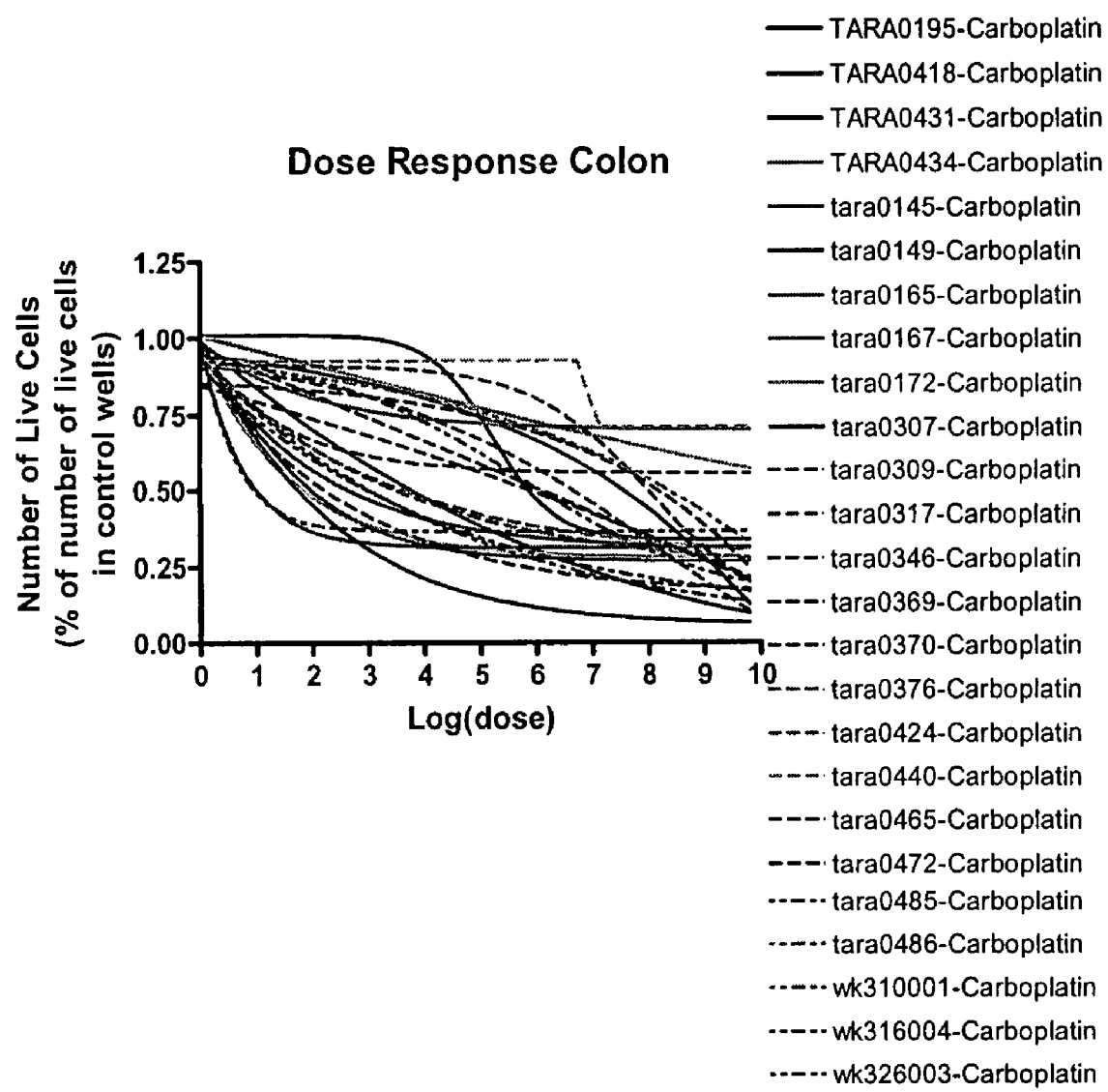
FIG. 3. Representative population distribution achieved during dose setting for Carboplatin on Colon tumor. Specimens are processed and cultured as described in the text. Wells of the microtiter plate are treated with decreasing concentrations from dose 10 to dose 1. Dose 0 is an untreated control well. Fraction cells surviving is determined by averaging three replicate wells at each dose divided by the average of the control well replicates. Each specimen is indicated by a different color line. Lines are non-linear curve fits of raw data.
Figure 4:
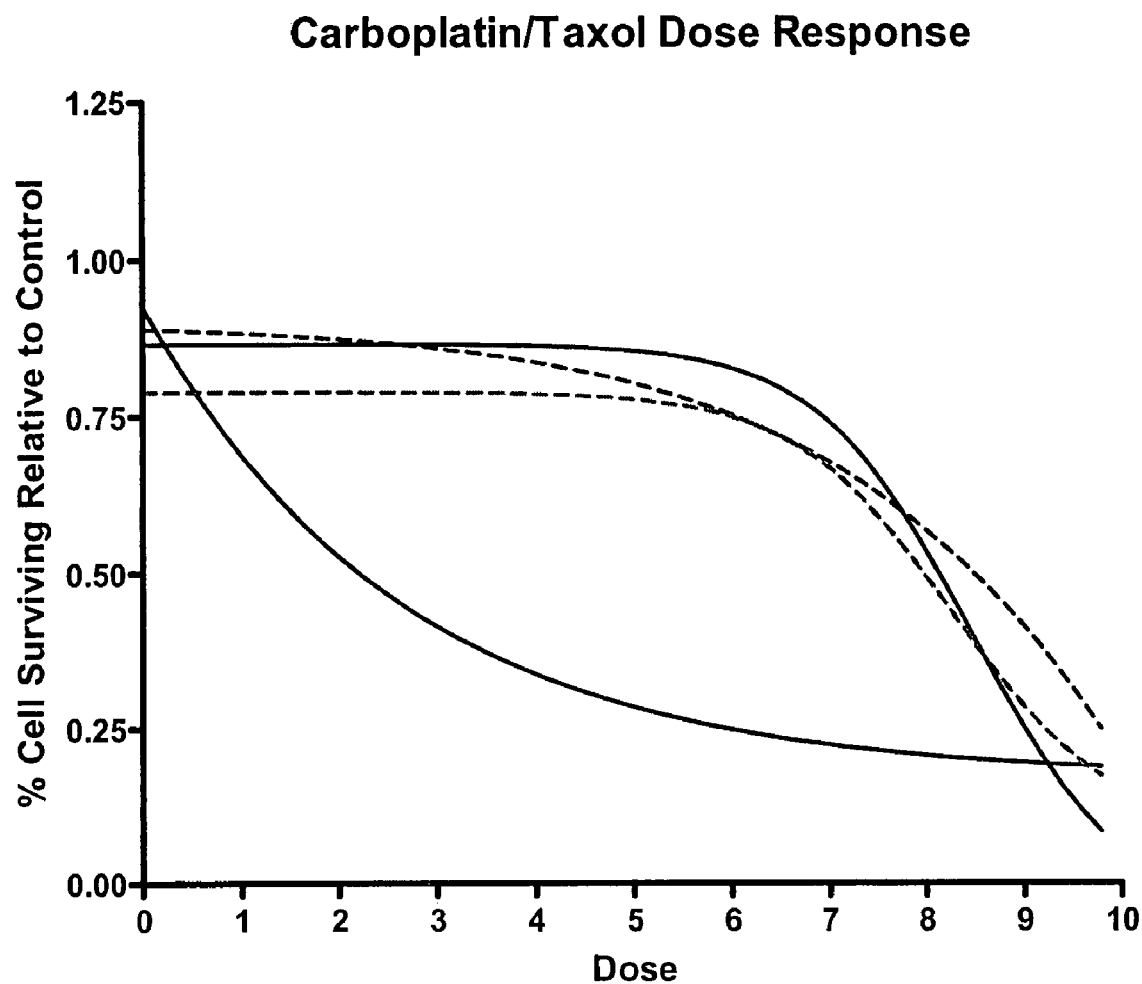
FIG. 4. Representative results for treatment of tumor derived cells with combination treatment of taxol and carboplatin. Specimens are processed and cultured as described in the text. Wells of the microtiter plate are treated with decreasing concentrations from dose 10 to dose 1. Dose 0 is an untreated control well. Fraction cells surviving is determined by averaging three replicate wells at each dose divided by the average of the control well replicates. Each specimen is indicated by a different color line. Lines are non-linear curve fits of raw data.

The following embodiments and aspects thereof are described and illustrated in conjunction with assays, methods, tools and systems included in the invention and are meant to be exemplary and illustrative, not limiting in scope. In various embodiments, one or more of the herein-described problems have been reduced or eliminated, while other embodiments are directed to improvements of the assays, methods, tools and systems described herein.

The invention includes a method of preparing a tumor cell sample comprising agitating a tumor explant to substantially release tumor cells from the tumor explant; culturing the released cells to produce a cell culture monolayer; and, forming a cell suspension from the monolayer cells before substantial phenotypic drift of the tumor cell population occurs. In one embodiment, the cell suspension is about 4,000 to 12,000 cells/ml. In another embodiment, the cell suspension is 4,000 to 9,000 cells/ml or 7,000 to 9,000 cells/ml. In another embodiment, the method further comprises inoculating cells from the cell suspension into at least one segregated site. In one aspect of the method, each segregated site comprises about $10^2$ to $10^4$ cells after the inoculating. In another aspect of the method, each segregated site comprises about $10^2$ to $10^3$ cells after the inoculating. In a different aspect of the method, each segregated site comprises about 200 to about 1000 cells. In yet another aspect, each segregated site comprises about 200 to about 500 cells.

Embodiments of the methods of the invention further comprise contacting the cells with at least one pharmaceutical agent. In one aspect of the method, the cells are cultured for about 4 to about 30 hours prior to contact with an agent. In another aspect, the method further comprises at least one combination treatment. In one aspect of the method, each combination treatment contacts the cells for about 25 to about 200 hours. In one aspect, each combination treatment comprises at least two agents. In another aspect, each combination treatment comprises a serial dilution series of 3-20 dose levels for each agent. The method further comprises adjusting the dose level of each agent to obtain from 0% up to and including maximal cell killing. In one aspect, each agent is initially used at a dose level below to above the range determined to be in the extracellular fluid surrounding a tumor in vivo. In another aspect, a dose response curve is generated for each agent. In one aspect of the method, cell viability is maintained for about 25 to about 200 hours.

In one embodiment of the method, media and nonadherent cells are removed at the end of about 25 to about 200 hours. In another aspect, the media and nonadherent cells are analyzed at the end of about 25-200 hours. In a different aspect, the adherent cells are analyzed at the end of about 25-200 hours. The adherent cells can be analyzed at any time or at any step in the procedures disclosed herein. In a variation of the method, the method is repeated at least once using cells which had been frozen after being grown in monolayers from explants.

The method also includes an automated cell imaging system which takes images of the cells using one or more of visible light, UV light and fluorescent light at predetermined intervals before, simultaneously with, or beginning immediately after, contact with each treatment. In a different embodiment, the cells are imaged after about 25 to 200 hours of contact with each treatment. In another embodiment, the cells are imaged once or multiple times, prior to or during contact with each treatment. Alternatively, UV or fluorescent light is used to take images to count cells. Visible, UV or fluorescent imaging can occur at multiple times prior to drug exposure, at predetermined intervals during drug exposure and at the end of the assay.

In a different embodiment, the method further comprises quantifying the number of viable or non-viable cells. In yet another aspect, the method comprises analyzing the genotypic or phenotypic state of the adherent cells after 25 to 200 hours. In one aspect of the method, the quantifying is by one or more of visible light, UV light and fluorescent light. In one embodiment of the method, the percent of cell confluency is determined.

In another embodiment, at least one pharmaceutical agent is a targeting agent. In a specific embodiment, the targeting agent targets a marker. In a more specific embodiment, the marker is selected from the group consisting of: markers of mesenchymal cells, epithelial cells, tumor markers and tissue specific markers. In another aspect, the marker is, but not limited to, one or more of: vimentin, desmin, S100, fibronectin and collagen, cell adhesion molecules and cytokeratins, tumor markers including but not limited to total levels and mutations in p53, cyclins, ras, src, growth factor receptors, hormone receptors, molecules involved in signal transduction and tissue specific markers including but not limited to CA125, PSA, PSM, milk proteins, surfactants and homeobox nuclear proteins.

Certain methods of the invention also further comprise assaying the cells of the cell suspension for the expression of at least one gene. In one aspect of the method, at least one gene is selected from the group consisting of ABCB1; ABCC1; ABCC2; ABCG2; ABL1; ACLY; ADH1A; ADPRT; ADSS; AKAP2; AKT1; AKT2; ALDH1A1; ALDH4; ANK3; ANXA8; AP2B1; APAF-1; APH-1A; API5; APOE; ATF5; ATP7B; B4-2; BAD; BAG1; BAK1; BARX2; BAX; BBC3; BCL2; BCL2L1; BCL2L2; BNIP3; BRCA1; BRCA2; BRF2; BTF3; BUB1; BUB3; C8orf2; CASP2; CBR1; CCNL2; CCNB1; CCNE2; CD44; CD68; CDA; CDC45L; CDK9; CEACAM6; CEGP1; CENPA; CES1; CFFM4; CFLAR; COL1A1; COL4A2; COX17; CPR2; CREM; CSNK2B; CTSL2; CUL1; CYP1B1; CYP2A6; CYP2B6; CYP2C8; CYP2C9; CYP2C19; CYP2D6; CYP3A4; CYP3A5; CYR61; DC13; DCK; DCTD; DD96; DDB1; DIA4; DLC1; DNAJD1; DPYD; DPYS; ECGF1; ECT2; EFEMP1; EGR1; EMP-1; EPB42; EPRS; ER; ERBB2; ERCC1; ERCC2; ERCC4; ERG; ESM1; EXT1; FAAH; FCGRT; FDXR; FGF18; FGFR2; FLJ10948; FLJ11190; FLJ11196; FLJ13855; FLJ14299; FLJ20323; FLJ20585; FLNA; FLT1; FN 1; GADD34; GADD153; GBX2; GJB1; GNAZ; GMPS; GRB7; GSR; GSTM1; GSTM3; GSTP1; GTF2H3; HBOA; HCFC1; HEC; HER2; HLA-C; HMG1; HN1; HSPC134; IGFBP5; IL4R; ISGF3G; ITGA5; Ki67; KIAA0175; KIAA0281; KIAA0303; KIAA1041; KIAA1067; KIAA1442; KIP2; KIT; KLK4; KNTC2; KPNA2; KRT13; L2DTL; LAMB1; LCHN; LDHA; LOC51061; LOX; MAD2L1; MAP2K4; MAP4; MAPT; MCM2; MCM6; MGMT; MGST1; MLH1; MMP9; MMP11; MP1; MPO; MSH2; MSN; MUC1; MYBL2; MYC; NDP; NFAT5; NFATC3; NFKB1; NME1; NME2; NMT1; NMU; NPM 1; NR1I2; ORC6L; ORM1/2; OXCT; p21/WAF; PAPPA; PB1; PCDHB2; PCSK7; PEC1; PGK1; PGR; PK428; PLD3; POLA2; POLB; POLE; POLH; POR; PP591; PPP2R1A; PRC1; PRKDC; PRPSAP1; PSME 1; PTK2; PTPRC; RAB6B; RAB11FIP1; RALGDS; RFC4; RNF2; RPL27; RRM1; RRM2; RTKN; SCARA3; SCUBE2; SEC61A1; SERF1A; SIAH2; SLC2A3; SLC7A10; SLC28A1; SLC28A2; SLC29A1; SLC29A2; SLC35B1; SM20; SOD1; SPARC; STK15; STOML1; SURF4; SURVIVIN; TBPL1; TCEB3; TDP1; TFRC; TGFB3; TIMP1; TIMP3; TLOC1; TNC; TNF; TNFSF6; TOP1; TOP2A; TP53; TRAG3; TUBB/TUBA2; TWIST; TXN; TYMS; UBE2M; UBCH10; UBPH; UCH37; UMP-CMPK; UMPS; UP; UPB1; USP22; WISP1; XIAP; XIST; XPA; XPB and XRCC1.

The methods of the invention also further comprise assaying the cells of the cell suspension for at least one SNP from at least one gene. In one aspect, the at least one gene is selected from the group consisting of ABCB1; ABCC1; ABCC2; ABCG2; ABL1; ACLY; ADH1A; ADPRT; ADSS; AKAP2; AKT1; AKT2; ALDH1A1; ALDH4; ANK3; ANXA8; AP2B1; APAF-1; APH-1A; API5; APOE; ATF5; ATP7B; B4-2; BAD; BAG1; BAK1; BARX2; BAX; BBC3; BCL2; BCL2L1; BCL2L2; BNIP3; BRCA1; BRCA2; BRF2; BTF3; BUB1; BUB3; C8orf2; CASP2; CBR1; CCNL2; CCNB1; CCNE2; CD44; CD68; CDA; CDC45L; CDK9; CEACAM6; CEGP1; CENPA; CES1; CFFM4; CFLAR; COL1A1; COL4A2; COX17; CPR2; CREM; CSNK2B; CTSL2; CUL1; CYP1B1; CYP2A6; CYP2B6; CYP2C8; CYP2C9; CYP2C19; CYP2D6; CYP3A4; CYP3A5; CYR61; DC13; DCK; DCTD; DD96; DDB1; DIA4; DLC1; DNAJD1; DPYD; DPYS; ECGF1; ECT2; EFEMP1; EGR1; EMP-1; EPB42; EPRS; ER; ERBB2; ERCC1; ERCC2; ERCC4; ERG; ESM1; EXT1; FAAH; FCGRT; FDXR; FGF18; FGFR2; FLJ10948; FLJ11190; FLJ1196; FLJ13855; FLJ14299; FLJ20323; FLJ20585; FLNA; FLT1; FN 1; GADD34; GADD153; GBX2; GJB1; GNAZ; GMPS; GRB7; GSR; GSTM1; GSTM3; GSTP1; GTF2H3; HBOA; HCFC1; HEC; HER2; HLA-C; HMG1; HN1; HSPC134; IGFBP5; IL4R; ISGF3G; ITGA5; Ki67; KIAA0175; KIAA0281; KIAA0303; KIAA1041; KIAA1067; KIAA1442; KIP2; KIT; KLK4; KNTC2; KPNA2; KRT13; L2DTL; LAMB1; LCHN; LDHA; LOC51061; LOX; MAD2L1; MAP2K4; MAP4; MAPT; MCM2; MCM6; MGMT; MGST1; MLH1; MMP9; MMP11; MP1; MPO; MSH2; MSN; MUC1; MYBL2; MYC; NDP; NFAT5; NFATC3; NFKB1; NME1; NME2; NMT1; NMU; NPM 1; NR1I2; ORC6L; ORM1/2; OXCT; p21/WAF; PAPPA; PB1; PCDHB2; PCSK7; PEC1; PGK1; PGR; PK428; PLD3; POLA2; POLB; POLE; POLH; POR; PP591; PPP2R1A; PRC1; PRKDC; PRPSAP1; PSME 1; PTK2; PTPRC; RAB6B; RAB11FIP1; RALGDS; RFC4; RNF2; RPL27; RRM1; RRM2; RTKN; SCARA3; SCUBE2; SEC61A1; SERF1A; SIAH2; SLC2A3; SLC7A10; SLC28A1; SLC28A2; SLC29A1; SLC29A2; SLC35B1; SM20; SOD1; SPARC; STK15; STOML1; SURF4; SURVIVIN; TBPL1; TCEB3; TDP1; TFRC; TGFB3; TIMP1; TIMP3; TLOC1; TNC; TNF; TNFSF6; TOP1; TOP2A; TP53; TRAG3; TUBB/TUBA2; TWIST; TXN; TYMS; UBE2M; UBCH10; UBPH; UCH37; UMP-CMPK; UMPS; UP; UPB1; USP22; WISP1; XIAP; XIST; XPA; XPB and XRCC1.

Definitions

As is generally the case in biotechnology and chemistry, the description of the present methods has required the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which the methods described herein belong. Definitions for other terms also appear elsewhere herein. However, the definitions provided here and elsewhere herein should always be considered in determining the intended scope and meaning of the defined terms. Other than in the operating examples or where otherwise indicated, all numbers or expressions referring to quantities of ingredients, reaction conditions, etcetera, used in the specification and claims are to be understood as modified in all instances by the term "about."

As used herein, the term "cancer" refers to a class of diseases of humans (and animals) characterized by uncontrolled cellular growth. As used herein, "cancer" is used interchangeably with the terms "tumor," "malignancy," "hyperproliferation" and "neoplasm(s)." The term "cancer cell(s)" is interchangeable with the terms "tumor cell(s)," "malignant cell(s)," "hyperproliferative cell(s)," and "neoplastic cell(s)" unless otherwise explicitly indicated. Similarly, the terms "hyperproliferative," "hyperplastic," "malignant" and "neoplastic" are used interchangeably, and refer to those cells in an abnormal state or condition characterized by rapid proliferation. Collectively, these terms are meant to include all types of hyperproliferative growth, hyperplastic growth, neoplastic growth, cancerous growths or oncogenic processes, metastatic tissues or malignantly transformed cells, tissues, or organs, irrespective of histopathologic type or stage of invasiveness.

As used herein, the term "candidate therapeutic agent" refers to an agent administered to a particular cell population causing a desired chemotherapeutic response.

As used herein, the term "cell culture" refers to cultures derived from dispersed cells taken from the original tissue or from a primary culture. It is not intended that the present invention be limited to cell cultures from any particular species, as the present invention finds use with any type of animal cell. See, for example, U.S. Pat. No. 6,528,309.

As used herein, the term "chemoresistant" refers to tumor cells (and interchangeable terms discussed, above) which show little or no significant detectable response to an agent used in chemotherapy.

As used herein, the term "chemosensitive" refers to tumor cells (and interchangeable terms discussed, above) which show a detectable response to an agent used in chemotherapy.

As used herein, the terms "chemotherapeutic agent," "cytotoxic agent," "anticancer agent" and "antitumor agent" are used interchangeably and refer to agents that have the property of inhibiting the growth or proliferation (e.g., a cytostatic agent), or inducing the killing, of tumor cells (and interchangeable terms as discussed above). The chemotherapeutic agent inhibits or reverses the development or progression of a cancer, such as for example, solid tumor, or a soft tissue tumor. See, for example, U.S. Pat. No. 6,599,912.

As used herein, the terms "chemotherapeutic response" and "chemoresponse" are used interchangeably. A chemoresponse refers to the response obtained upon administration of a pharmaceutical agent. The desired chemoresponse may be a genotypic response, such as, for example, a change in expression of one or more genes, for example. The desired chemoresponse may also be a phenotypic response, such as, for example, the slowing of, or regression of, the growth of tumor cells. Upon identification of a chemotherapeutic agent giving a desired chemoresponse in the assays or methods disclosed herein, the agent is then administered to the patient in vivo. In one embodiment of the methods disclosed herein, the tumor cell population is a chemoresistant cell population and the desired chemoresponse is slowing of, death or regression of the chemoresistant cells.

As used herein, the term "chemotherapy" refers to administration of at least one chemotherapeutic agent to patients having a cancer.

As used herein, the term "combination treatment" refers to a treatment of the cells with at least two pharmaceutical agents. The pharmaceutical agents which are used either at the same time, or separately, or sequentially, according to the methods disclosed herein, do not represent a mere aggregate of known agents, but a new combination with the surprising valuable property that modifies the chemoresistance and/or chemosensitivity of the tumor cells and allows a new effective treatment (partial or complete response) for cancer.

As used herein, the term "contacting" refers to the interaction of the tumor cells and at least one pharmaceutical agent.

As used herein, the term "Cytotoxicity Index" (CI) is the ratio of the number of treated cells to number of control cells (e.g., untreated cells) after treatment with an agent. A "normalized Cytotoxicity Index" is a CI that has been corrected to take into account variations in the assay such as variations in the starting number of cells.

As used herein, the term "effective amount" of a compound refers to a sufficient amount of the drug or agent which provides the desired effect.

As used herein, the term "empiric chemotherapy" refers to selecting chemotherapy based on outcomes reported in the literature for groups of patients with a particular type of tumor.

As used herein, the term "epithelial cell marker" refers to a marker expressed by epithelial cells. As used herein, the term "malignant epithelial cell marker" refers to a marker expressed by malignant epithelial cells. Many are known in the art and optionally intended for use as part of, or in conjunction with the assays, methods, tools and systems as included in the invention disclosed herein. Epithelial cell markers, malignant or nonmalignant, may be used as markers for aid in determining whether phenotypic drift and/or genotypic drift has occurred in the cultured tumor cell population at any point during the cell culture period.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "marker" refers to any genotypic or phenotypic characteristic of a cell or cell population that, alone or in combination with other marker(s), can be used to identify the particular cell type. Markers can be, without limitation, genotypic, such as an insertion, deletion or substitution, or phenotypic, such as the presence of high levels of a receptor or a secreted peptide. A marker may be a molecular predictor of response. For example, a molecular predictor of response such as EGR1, a gene involved in cell proliferation, may also be useful as a marker in identifying a particular cell type. The marker can be any molecule detectable on the surface of tumor cells, in tumor cells or both. Thus, the marker is any one or more of a protein, a lipid, a carbohydrate, a nucleic acid and any combination thereof (for example, a glycoprotein). The marker may or may not be expressed in tumor cells and therefore is typically evaluated prior to initiating chemotherapy.

As used herein, the term "maximal cell killing" refers to the cytotoxic index associated with the greatest amount of cell kill for a given chemotherapeutic agent that is maintained over at least 2 of the highest doses tested (Doses 9 and 10). Most agents do not kill all (100%) of the tumor cell population. Cytotoxic chemotherapeutic agents exert fractional cell kill whereby a constant fraction, and not number, of the live tumor cells are killed such that 100% tumor cell kill is only asymptotically approached but rarely achieved. Cytostatic chemotherapeutic agents halt the proliferation of tumor cells but are ineffective at killing tumor cells so that 100% of the tumor cells are not killed.

As used herein, the term "molecular predictor of response" refers to at least one gene in a pathway such as, for example, chemotherapeutic drug metabolism (such as, for example, CYP3A4, CYP3A5, CYP2D6, CYP2C8 and CYP2C9), drug transport (such as, for example, ABCB1, ABCC1, ABCC2 and ABCG2), cell apoptosis (such as, for example, BCL2, BAD, BAX and BAK1), cell proliferation (such as, for example, EGR1, CYR61, p21/WAF and TP53) and DNA repair pathways (such as, for example, ERCC1, ERCC2, MLH1 and MSH2). A molecular predictor of response is predictive of whether the patient is likely to respond favorably to a chemotherapeutic regimen comprising a given agent or given combination therapy or whether long term survival of the patient following termination of chemotherapy or other treatment is likely.

As used herein, the term "neoadjuvant treatment" refers to administration of chemotherapy prior to surgical intervention or resection. Neoadjuvant treatment may be used optionally in conjunction with any of the assays, methods, tool or systems disclosed herein. For example, the patient may receive neoadjuvant treatment before a tumor biopsy is obtained from the patient.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19:5081; Ohtsuka et al., 1985, J. Biol. Chem. 260:2605-2608; Cassol et al., 1992; and Rossolini et al., 1994, Mol. Cell. Probes 8:91-98). The term nucleic acid is used interchangeably with gene, cDNA, and mRNA encoded by a gene.

As used herein the terms "optional" or "optionally" means that the subsequently described circumstance may or may not occur, so that the description includes instances where the circumstance occurs and instances where it does not.

As used herein, the term "pharmaceutical agent" includes, without limitation, biologically active molecules, enzymes, proteins, lipids, carbohydrates, glycoproteins, glycolipids, nucleic acids such as DNA and/or RNA and fragments of DNA and/or RNA, antisense nucleic acids, siRNA molecules, antibodies, small molecules and inorganic pharmaceutical molecules. As used herein, "small molecules" are those molecules having a molecular weight of about 2000 Daltons or less. The term "pharmaceutical agent" is used interchangeably with the terms "agent," "drug," "compound," "therapeutic," "chemotherapeutic," and "biological agent" herein.

The term "pharmaceutical agent" encompasses not only the specified molecular entity but also its pharmaceutically acceptable, pharmacologically active analogs, including, but not limited to, salts, esters, amides, prodrugs, conjugates, active metabolites and other such derivatives, analogs and structurally, biologically and functionally related compounds. The agents or derivatives thereof disclosed herein are in a pharmaceutically acceptable carrier when necessary, i.e., when required by a method or assay. More than one agent can be simultaneously used at a time. For example, combination treatment may comprise two or three or four or more pharmaceutical agents used together.

As used herein, the term "pharmaceutically acceptable" refers to a material that is not biologically or otherwise undesirable, i.e., the material may be incorporated into a pharmaceutical composition without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

As used herein, the term "phenotypic drift" refers to phenotypic plasticity, which is a phenomenon in which a given genotype may develop different states for a character or group of characters in different environments, the phenotypic variability produced by a given genotype under the range of environmental conditions common to the natural habitat of the species or under the standard culture or experimental conditions. (A Dictionary of Genetics, 5th edition, King et al., Oxford University Press, NY Oxford 1997). Phenotypic drift may also include changes in a cell character or a group of characters due to a genetic change. "Substantial phenotypic drift" refers to a detectable change in the character or nature of one or more biochemical markers, functional markers or physical markers characteristic of a tumor cell; and/or to a change in one or more molecular predictors of response. The change is detected using any detection method known in the art including morphometry by cell shape changes and the epithelial markers discussed herein. Changes in fibroblast markers, malignant markers, proliferation markers can also be detected using detection methods known in the art.

As used herein, the term "predicting the chemoresponse" refers to any method of analyzing the response of tumor cells contacted with at least one pharmaceutical agent. Methods for evaluating the molecular chemoresponse include expression assays (microarrays, PCR-based technology) disclosed herein and other assays known to those of skill in the art. In one embodiment of the invention, evaluating the chemoresponse comprises performing an analysis of the expression of one or more molecular predictors of response. In another embodiment of the invention, evaluating the chemoresponse comprises counting the cells before and after treatment with an agent and calculating a Cytotoxicity Index (CI).

As used herein, the term "primary culture" refers to a culture that has been developed from a patient's tumor cells and before the first subculture. Thus, a primary culture represents the first in vitro growth of cells. It is not intended that the present methods be limited to primary cultures from any particular species, as the present invention finds use with any type of animal cell. See, for example, U.S. Pat. No. 6,528,309. It is not intended that the present invention be limited to primary cultures but may include first or subsequent subcultures.

As used herein, the term "SNP" (single nucleotide polymorphism) refers to nucleotide sequence variations that occur when a single nucleotide (A, T, C or G) in the genome sequence is altered. SNPs can occur in both coding (gene) and noncoding regions of the genome. Many SNPs have no effect on cell function while other SNPs predispose people to cancer or a disease or influence their response to a drug or are linked to a locus that predisposes a person to cancer or a disease or influences their response to a drug. Such linkages can be determined by any commonly available means such as those procedures that produce linkage disequilibrium maps for a given SNP or a group of SNPs.

As used herein, "staining" refers to any number of processes known to those in the field that are used to allow visualization and/or improve visualization of cell component(s) and/or feature(s). Many such processes are publicly available and known to those of skill in the art and may optionally be used in or in conjunction with the assays, methods, tools and systems disclosed herein. Many stains or other molecules allowing visualization of the cells and/or cell features are known in the art and may optionally used in or in conjunction with the assays, methods, tools and systems disclosed herein.

As used herein, the term "substantially release tumor cells" refers to the number of tumor cells released from the explant upon sudden agitation or motion of the explant. This releases a significant number of viable and representative tumor cells from the explant as compared to the number released if the explant is not subjected to sudden agitation or motion. This process may be facilitated with the use of chemicals or enzymes designed to enhance the release of tumor cells from tissue segments.

As used herein, the term "targeting agent" refers to an agent designed to target a marker expressed in tumor and nontumor cells, on tumor and nontumor cells or both in and on tumor and nontumor cells. Targeting agents useful in the practice of the methods disclosed herein include antibodies, cell surface ligands, nucleic acids, etcetera. Targeting agents are also useful for tracking changes in markers during culture and for determining the occurrence of phenotypic and/or genotypic drift. Many targeting agents are known to those of skill in the art and are optionally used in, or in conjunction with, the assays, methods, systems and tools described herein. The targeting agent may itself be detectable by any method known in the art, such as for example, by radioactive labeling, linkage to fluorescent molecules or linkage to other molecules which are detectable.

I. General Overview

In one embodiment of the methods disclosed herein, a tissue sample from the patient is harvested, cultured and separately exposed to a plurality of treatments and/or therapeutic agents for the purpose of objectively identifying the effective treatments for the cultured cells obtained from the patient. The culture techniques of the present methods also result in a monolayer of cells that express cellular markers, secreted factors and tumor antigens in a manner representative of their expression in vivo. The culture techniques of the present methods also allow for monitoring of tumor antigen expression or other tumor markers in order to detect possible phenotypic and/or genotypic drift by the cultured tumor cells in order to ascertain whether in vitro tumor antigen expression is correlative of, or similar to, in vivo tumor antigen expression. Specific methods disclosed herein, such as tissue sample preparation techniques, render this method practically as well as theoretically useful. See, for example, U.S. Pat. Nos. 5,728,541; 6,887,680 and 6,416,967.

The ChemoFx Assay® disclosed herein may include the use of a predictive algorithm of patient response to chemotherapy by evaluating tumor factors via the response of patient-derived tumor cells to various chemotherapeutic agents in vitro. Furthermore, the incorporation of host factors (in the form of genomic or phenotypic markers) into the algorithm further enhances its predictive ability. The invention includes a method of predicting chemotherapeutic response of patient tumor cells to at least one therapeutic agent comprising assaying expression levels of at least one gene selected from the group consisting of genes involved in chemotherapeutic drug metabolism, in drug transport, in cell apoptosis, in cell proliferation, and in DNA repair, in the patient tumor cells. The invention also includes a method of predicting chemotherapeutic response of patient tumor cells to at least one therapeutic agent comprising detecting at least one SNP from at least one gene selected from the group consisting of genes involved in chemotherapeutic drug metabolism, in drug transport, in cell apoptosis, in cell proliferation, and in DNA repair, in the patient tumor cells.

II. ChemoFx® Assays: Version 1 and Version 2

The proprietary ChemoFx® Assays disclosed herein involve the isolation, short-term growth, and drug dosage treatment of epithelial cells derived from solid tumors. At the time of surgical "debulking," or biopsy (e.g., vacuum-assisted and core biopsy) or fine needle aspiration of a tumor site, pieces of solid tumor are obtained by the surgeon, radiologist, or pathologist and placed in tissue culture media. The tumor is minced into small pieces and placed with cell culture media (Lifetech, Gibco BRL) into small flasks or other appropriately sized culture dishes for cell outgrowth. Over time, cells move out of the tumor pieces and form a monolayer on the bottom of the vessel. Once enough cells have migrated out of the ex vivo explant pieces, they are then trypsinized and reseeded into microtiter plates for either ChemoFx® Assay (versions 1 and 2 described below) or for immuno-histochemistry (IHC) analysis.

A. Version 1

In Version 1 of the ChemoFx® Assay, cultured cells are seeded into 60 well microtiter plates at a density of about 100-500 cells per well and allowed to attach and grow for about 24 hours. After about 24 hours in culture the cells are then exposed for about 2 hours to a battery of chemotherapeutic agents. At the end of the incubation with the chemotherapeutic agents, the plates are washed to remove non-adherent cells. The remaining cells are fixed with 95% ethanol and stained with the DNA intercalating blue fluorescent dye, DAPI, or 6-diamidino 2-phylindole dihydrochloride (Molecular Probes, Eugene, Oreg., USA) or equivalent. The surviving cells are then counted using an operator-controlled, computer-assisted image analysis system (Zeiss Axiovision, Thornwood, N.Y., USA). A cytotoxic index is then calculated using methods known in the art. The data are presented graphically as the cytotoxic index (CI). A dose-response curve is then generated for each drug or drug combination evaluated.

B. Version 2

For the Version 2 ChemoFx® Assay, proprietary software, named Resource Allocator, is utilized to generate logical scripts that direct the activity of a liquid handling machine. The procedure, however, may be carried out using any liquid handling machine with appropriate software, known in the art. This software employs the ideology behind the assay, a plating cell suspension of about 4,000 to 12,000 cells/ml and 1-10 replicates per dose for each of a multiple dose drug treatments, to calculate the number of cells necessary to accommodate testing of all requested drugs. In one embodiment, the assay comprises about 8,000 cells/ml and 3 replicates per dose for each of 10 dose drug treatments. After those calculations are complete, Resource Allocator will determine the quantity of disposable pipette tips, 8 row deep-well basins and 384 well microplates necessary for cell plating as well as the location of those consumables on the stage of the liquid handler. Finally, Resource Allocator will determine the specific location of cells in an 8 row deep-well basin prior to plating, and the specific location of cells in a 384 well microplate after plating. This information is provided in a printable format for easy interpretation of results. Using the information provided by Resource Allocator, a cell suspension is prepared at a concentration of about 4,000 to 12,000 cells/ml and delivered to a reservoir basin on the stage of the liquid handling machine. The machine then seeds about 200 to 400 cells in about 30 to 50 µl of medium into the wells of a 384 well microplate in replicates of about 1-10, after which the cells are allowed to adhere to the plate and grow for about 24 hours at 37° C. In one embodiment, the cell suspension is prepared at a concentration of about 8,000 cells/ml, and the liquid handling machine seeds about 320 cells in about 40 µl of medium into the wells of a microplate in replicates of 3.

After all cell suspensions have been delivered to the appropriate 384 well microplate, Resource Allocator is initiated again to calculate the number of drugs, and volume of each, that are needed to accommodate treatment of all cells plated. The software uses a volume of about 30-50 µl per replicate for each dose of a drug treatment and the number of unique cell lines needing that particular treatment to calculate the total volume of drug required. For instance, in one embodiment, the software uses a volume of about 40 µl per replicate for each dose. After determining the necessary volume of each drug, the software calculates the number of disposable pipette tips, 96 well deep-well plates, and medium basins necessary for drug preparation. Resource Allocator will then determine into which 96 well deep-well plate each drug will go, the specific location in a 384 well microplate the treatment will be delivered, and the stage location for all of the consumables. For ease of interpretation, Resource Allocator provides these results in a printable format.

Following the approximately 4-28 hour incubation of the cell plates, the liquid handling machine prepares ten doses of each drug, in the appropriate growth medium, via serial dilutions in a 96 well deep-well microplate. When the drugs are ready, the liquid handling machine dispenses 30-50 µl of a drug (at 2× the final testing concentration) into the appropriate wells of the deep well plate. After treatment, the drugs can be left on the cells for an incubation of about 25-200 hours thus necessitating their preparation in growth medium. In one embodiment of the invention, the drugs are left on the cells for an incubation of 48-96 hours. During this period, cell viability is maintained with a standard incubator. During imaging of the cells, their viability is maintained with a device named the BioBox and visible light images are taken at predetermined intervals using proprietary software named Plate Scanner. The BioBox is a humidified incubator environment on the stage of a microscope. While the procedure uses the BioBox, other equipment known in the art may be used in practice. Temperature and gas composition are maintained at 37° C. and 5% $CO_2$ with air balance, respectively. It serves the purpose of providing an environment suitable for cell growth, while maintaining limited exposure to ambient air, which reduces potential contamination of the plates. Plate Scanner automates the acquisition of images from each well that has received cells in a microtiter plate. Plate Scanner provides the ability to choose which wavelengths of light to use as well as the ability to decide exposure duration for each wavelength of light chosen. In addition, the software uses focal stack imaging to determine the physical geometry of each plate in order to optimize image quality. The software automatically alters the light (either visible, UV or fluorescent) to capture the necessary image and stores the image on a hard drive. While the procedure uses Plate Scanner, other equipment and software known in the art may be used in practice.

At the end of the 25-200 hour incubation period, the liquid handling machine is used to remove the media and any non-adherent cells. Then, the remaining cells are fixed for at least 20 minutes in 95% ethanol followed by the DNA intercalating blue fluorescent dye, DAPI. Following fixation and staining, the automated microscope is used to take visible and UV images of the stained cells in every well. Afterwards, the number of cells per well in both visible and UV light is quantified using proprietary software named Cell Counter.

Cell Counter scans through each unique image and ascertains the cell locations by measuring the peak pixel intensity and aggregating pixels that are significantly above the background signal. The software provides various filters, such as minimum pixel intensity threshold, which allow better distinction of cells from background noise. While the procedure uses Cell Counter, any cell counting machine known in the art may be used in the practice of the methods of the inventions disclosed herein.

A complete dose response curve is generated for each drug evaluated. An Image analysis system is used in analysis of the cells. Here, cells grown in plates are imaged using equipment and methods known to those of ordinary skill in the art.

Modification of ChemoFx® assays, disclosed herein, are within the ordinary skill in the art. Inclusion of other assays, methods, procedures, tools, materials, drugs, systems, compounds and equipment (such as for example, liquid handling machines and the operating software) known in the art is intended to be an option in the practice of the assays, methods, tools and systems included in the invention disclosed herein.

In the agent assays, growth of cells is monitored to ascertain the time to initiate the assay and to determine the growth rate of the cultured cells; sequence and timing of agent addition is also monitored and optimized. By subjecting uniform samples of cells to a wide variety of pharmaceutical agents (and concentrations thereof), the most efficacious agent or combination of agents can be determined.

For assays concerning cancer treatment, a two-stage evaluation may be carried out in which both acute cytotoxic and longer term inhibitory effects of a given anti-cancer agent (or combination of agents) are investigated. Thus, a comprehensive and integrated system for identifying, tracking and analyzing an individual patient's malignancy through the duration of the malignancy and thereafter is provided. The duration of the malignancy is intended to cover both the initial cell culture and determination, using one or more of the assays or methods disclosed herein, of agents as well as the culture of chemoresistant cells and determination, using one or more of the assays or methods disclosed herein, of agents effective to affect the progress of the malignancy.

The commercial potential of the assays, methods, tools and systems disclosed herein is considerable for many reasons, but most notably because it minimizes the number of valuable patient cells necessary to generate dose response information, the system optionally uses a nearly automated system for data accrual that requires very little user intervention and data generated from the assays disclosed herein can be used with a software package to generate patient dose response information.

"Cancer" as used herein, includes, without limitation, ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, kidney cancer, liver cancer, malignant peritoneal effusion, malignant pleural effusion, melanoma, mesothelioma, multiple myeloma, neuroblastoma, non-Hodgkin's lymphoma, osteosarcoma, penis cancer, prostate cancer, retinoblastoma, soft-tissue sarcoma, squamous cell carcinomas, stomach cancer, testicular cancer, thyroid cancer, trophoblastic neoplasms, vaginal cancer, cancer of the vulva, Wilm's tumor and malignancies. Also included in the term "tumor" or "tumor cell(s)" are solid tumor cells, a soft-tissue tumor cell, a metastatic tumor cell, a leukemic tumor cell, and a lymphoid tumor cell. The cancer may be a fibrosarcoma, myosarcoma, liposarcoma, chondrosarcoma, osteogenic sarcoma, chordoma, angiosarcoma, endotheliosarcoma, lymphangiosarcoma, lymphangio-endotheliosarcoma, synovioma, mesothelioma, leiomyosarcoma or rhabdomyosarcoma, epithelial carcinoma, glioma, astrocytoma, medullobastoma, craniopharyngioma, ependymoma, pinealoma, hemangioblastoma, acoustic neuroma, oligodendroglioma, meningioma, melanoma, neurobastoma, retinoblastoma, leukemia, lymphoma, or Kaposi sarcoma. See, for example, U.S. Pat. No. 6,884,907.

III. Cell Culture Methods

When a patient is to be treated for the presence of tumor, in the preferred embodiment of the present methods, a tumor biopsy of about 15 mg or more of non-necrotic, non-contaminated tissue is harvested from the patient by any suitable biopsy or surgical procedure known in the art. For instance, a tumor biopsy of about 15 mg, about 20 mg, about 25 mg, about 30 mg or about 35 mg or more can be used. In one embodiment of the invention, the biopsy sample is about or greater than 25 mg. In another embodiment, the biopsy sample is at least about 15 to about 35 mg. Tumor sample processing generally proceeds as follows under a Laminar Flow Hood. Reagent grade ethanol is used to wipe down the surface of the hood prior to beginning the sample preparation. The tumor is then removed, under sterile conditions, from the shipping container using sterile forceps and placed in a sterile petri dish where it is systematically minced by using two sterile scalpels in a scissor-like motion, or mechanically equivalent manual or automated opposing incisor blades. This cross-cutting motion is important, but not necessary, because the technique creates smooth cut edges on the resulting tumor multicellular particulates. In one embodiment, the tumor particulates measure 0.25 $mm^3$ to 1.5 $mm^3$. For instance, the tumor particulates can measure about 0.25 $mm^3$, 0.30 $mm^3$, 0.40 $mm^3$, 0.50 $mm^3$, 0.60 $mm^3$, 0.70 $mm^3$, 0.75 $mm^3$, 0.80 $mm^3$, 0.90 $mm^3$, 1 $mm^3$, 1.1 $mm^3$, 1.2 $mm^3$, 1.25 $mm^3$, 1.30 $mm^3$, 1.40 $mm^3$, or 1.50 $mm^3$. Preferably but not necessarily, the tumor particulates each measure approximately 1 $mm^3$.

In one embodiment, the particles are then agitated to substantially release tumor cells from the tumor explant particles. Such agitation includes any mechanical means that enable the enhanced plating of tumor cells and includes, but is not limited to, shaking, swirling, or rapidly disturbing the explant particles. These procedures may be done by hand by, for instance, sharply hitting the container against a solid object or by the use of mechanical agitation. For instance, a standard vortex mixer may be used. This agitation step typically increases the number of adherent tumor cells by at least about 5%, 10%, 20% 30%, 40%, 50%, 60%, 70%, 80%, 90%, 100%, 200%, 300% (and including any percentage in between) or more compared to non-agitated replicate samples after about 12-48 hours or more of incubation. Chemicals or enzymes may be employed to facilitate the release of tumor cells from the tumor explant. Enzymatic agitation with enzymes which may include, but are not limited to, collagenase, DNase or dispase, is also included as an optional step in the practice of the procedures disclosed herein.

After each tumor has been minced to particles about 1 $mm^3$ or less, the particles are plated in culture flasks using sterile pasteur or serological pipettes (approximately 9 explants per T-25 or 20 particulates per T-75 flask). Each flask is then labeled with the patient's code, the date of explantation and any other distinguishing data. The explants should be evenly distributed across the bottom surface of the flask, with initial inverted incubation in a 37° C. incubator for 5-10 minutes, followed by addition of about 5-10 ml sterile growth medium and further incubation in the normal, non-inverted position. Flasks are placed in a 37° C., 5% $CO_2$ incubator. Flasks should be checked daily for growth and contamination. Over a period of approximately a few days to a few weeks, with weekly removal and replacement of about 5 ml of growth medium, the explants will foster growth of cells into a monolayer.

In another embodiment, after mincing and transferring the particles to one or more labeled flasks, the tumor explants are exposed to a cocktail containing Collagenase II and DNase. In one aspect of the invention, the cocktail contains 0.25% Collagenase II and 0.001% DNase. In another aspect of the invention, the cocktail contains about 0.025% Collagenase II and 0.001% DNase.

The amount of collagenase and DNase can be varied to achieve the desired beneficial outcome(s) as herein described, for instance, enzymes concentrations can include about 0.010% collagenase to about 0.60% collagenase and about 0.0007% DNase to about 0.005% DNase. The amount of Collagenase II required by the methods of the present invention is the amount necessary to reduce the size of a tumor explant when used in conjunction with DNase or the amount required to provide the advantageous results herein discussed. For instance, the Collagenase II and DNase solution to which the tumor explants are exposed can contain about 0.010% or less Collagenase II, about 0.025% or less Collagenase II, about 0.050% or less Collagenase II, about 0.075% or less Collagenase II, 0.10% or less Collagenase II, about 0.15% or less Collagenase II, about 0.20% or less Collagenase II, about 0.25% or less Collagenase II, about 0.30% Collagenase II, about 0.35% Collagenase II, about 0.40% Collagenase II, about 0.45% Collagenase II, about 0.50% Collagenase II or about 0.60% or more Collagenase II (or about 0.15% to 0.6% final concentration). In one embodiment, the Collagenase II and DNase solution contains less than about 0.30% Collagenase II, less than about 35% Collagenase II, less than about 40% Collagenase II, less than about 45% Collagenase II or less than about 50% Collagenase II. For instance, about 0.25% Collagenase and 0.001% DNase can be used to process ovarian tumor tissue samples and about 0.025% Collagenase and 0.001% DNase can be used to process colorectal tumor tissue samples. The terms "cocktail," "solution," and "composition" are used interchangeably herein when referring to the use of a collagenase and DNase solution. As used herein, "collagenase" and "Collagenase II" are used interchangeably.

The amount of DNase required by the methods of the present invention is the amount necessary to reduce the size of a tumor explant when used in conjunction with Collagenase II or the amount required to provide the advantageous results described herein. For instance, the Collagenase II and DNase solution can contain about 0.0007% or less DNase, about 0.0008% DNase, about 0.0009% DNase, about 0.001% DNase, about 0.002% DNase, about 0.003% DNase, about 0.004% DNase or about 0.005% or more DNase (or about 0.0007% to 0.005% final concentration).

The Collagenase II and DNase solution can comprise Collagenase II and DNase diluted in cell culture media. In one embodiment of the invention, Collagenase II and DNase are diluted in Hank's Balanced Salt Solution (HBSS) media with or without $Ca^{2+}$ and $Mg^{2+}$. A skilled artisan would appreciate that various types of tissue culture media can be used to dilute Collagenase II and DNase. For instance, a cell culture media such as HBSS which is not a growth medium can be used. Conversely, growth medium can be used. Also, cell type can influence or dictate the type of media used.

The Collagenase II and DNase cocktail of the invention can optionally contain compounds to reduce the likelihood of microbial contamination. For instance, the composition can contain one or more antibiotics, including, but not limited to, gentamicin, streptomycin, kanamycin and penicillin. The composition can also contain one or more fungicides, including, but not limited to, nystatin and amphotericin B.

The tumor explants treated with a Collagenase II and DNase cocktail can be incubated under conditions appropriate for the cell type. For instance, the effect of treatment may be enhanced by incubating the tissue explant for about 3 minutes, about 5 minutes, about 10 minutes, about 15 minutes, about 20 minutes, about 25 minutes, about 30 minutes, about 35 minutes, about 40 minutes, about 45 minutes, or about an hour or more with the Collagenase II and DNase cocktail. Incubation coupled with gentle agitation may further increase the release of cells from the treated tissue explants. Cells can be mechanically agitated by gently shaking cells on a shaker during incubation.

After the treatment of tumor explants with Collagenase II and DNase, explants should preferably be washed one or more times to remove the enzymes. Cells can be washed by methods known in the art such as by adding cell culture media to explants, centrifuging explants, and removing the resulting supernatant. It may be necessary to wash cells two or three times to remove the Collagenase II and DNase.

The use of both of the above procedures to form a cell monolayer culture maximizes the growth of malignant cells from the tissue sample, and thus optimizes ensuing tissue culture assay of chemotherapeutic action of various agents to be tested.

A. Primary Culture

Once a primary culture is established from a patient's malignancy, the primary culture can be maintained without any treatments beside normal feedings, as indicative of the growth of the malignancy absent treatment with a therapeutic regimen. Subcultures of the primary culture are prepared so that the cells of the primary culture are not affected by any subsequent testing or treatments. Although the primary culture is preferably left untreated, either the primary culture or a subculture thereof can be propagated as a reference culture. The reference culture is a culture which is treated with an agent or agents reflective of a patient's actual treatment regimen. For instance, if a patient is treated with a pharmaceutical agent, the reference culture is treated with the same agent in the same concentration. The reference culture can be monitored genotypically or phenotypically, using molecular predictors of response or markers, to reflect actual progress of the malignancy in the patient. Treatment of the reference culture need not be limited to anticancer therapies, but can reflect all of a patient's treatments. For instance, and without limitation, thrombolytic or anti-thrombogenic treatments, can be applied to the reference culture to reflect a patient's treatment.

Subcultures of either the primary culture or the reference culture can be used for further analysis. Preferably, since the reference culture is indicative of the current state in a patient of a malignancy, subcultures of the reference culture are analyzed. At various points in the passage of the control culture and the reference culture, aliquots of cells from those cultures can be stored cryogenically, or otherwise.

B. Tissue Explants

The explant is removed prior to the emergence from the explant of a substantial number of non-target cells, resulting in a monolayer of cells that is enriched for a tumor cell population of interest. For example, it has been discovered that cells emerge as a monolayer from a culture tumor tissue explant in an orderly fashion, the tumor cells emerging first, followed by stromal cell populations. If the tumor cell explant remains in culture, the stromal cells have been found to dominate the tumor cells in culture. This creates a culture that is enriched from non-target stromal cells and that is not reflective of the in vivo cell population. Thus, in a tumor cell culture, the explant is removed from the growth medium prior to the emergence of a substantial number of stromal cells from the explant. The time at which an explant is removed from its culture medium depends upon the type of cell being cultured, the rate of emergence of various cell types and the desired purity of the resulting cell culture monolayer. This can be determined empirically for a given cell type. In the case of tumor cells, the multicellular tissue explant is preferably removed when the cell culture monolayer is at about 10 to about 50 percent (or more) confluent. In one aspect of the method, the multicellular tissue explant is removed at about 15 to about 25 percent confluency. In another aspect of the method, the explant is removed at about 20 percent confluency. Percent confluency is the estimate of the area occupied by the cells divided by the total area in an observed field.

One method of minimizing phenotypic and/or genotypic drift in cultures is to limit the passaging of cells and testing the cells at the earliest moment of reaching clinical number. Occasionally, explants are "replanted" in another culture as a rescue technique if the first culture was not successful.

C. Methods of Determining Cell Viability

Enhanced growth of actual tumor cells is only one aspect of the present methods. A growth rate monitoring system may also be used to oversee growth of the monolayer once formed. Once a primary culture and its derived secondary monolayer tissue culture have been initiated, the growth of the cells is monitored to ascertain the time to initiate the chemotherapy assays and to determine the growth rate of the cultured cells.

Monitoring of the growth of cells is conducted by counting the cells in the monolayer on a periodic basis, without killing or staining the cells and without removing any cells from the culture flask. The counting may be done visually or by automated methods, either with or without the use of estimating techniques known in the art (counting in a representative area of a grid multiplied by number of grid areas, for example). Data from periodic counting is then used to determine growth rates which may or may not be considered parallel to growth rates of the same cells in vivo in the patient. If growth rate cycles can be documented, for example, then dosing of certain active agents can be customized for the patient. It should be noted that with the growth rate determinations conducted while the monolayers grow in their flasks, the present method requires no hemocytometry, flow cytometry or use of microscope slides and staining, with all their concomitant labor and cost, although such methods are optionally included in the practice of the methods included in the invention disclosed herein.

Protocols for monolayer growth rate generally use a phase-contrast inverted microscope to examine culture flasks incubated in a humidified 37° C. (5% $CO_2$) incubator. When the flask is placed under the phase-contrast inverted microscope, ten fields (areas on a grid inherent to the flask) are examined using the 10× objective, with the proviso that the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two or among three or more (monitoring cell viability) flasks, an average cell count for the total patient sample should be calculated.

The calculated average percent confluency should be entered into a process log to enable compilation of data, and plotting of growth curves, over time. Monolayer cultures may be photographed to document cell morphology and culture growth patterns. See, for example, U.S. Pat. Nos. 5,728,541; 6,887,680 and 6,416,967 and U.S. patent application Ser. Nos. 09/040,161; 09/039,957; 09/095,993; 09/691,492 and 60/616,851.

D. Segregated Sites

The performance of the chemosensitivity assays used for screening purposes depends on the ability to deliver a reproducible cell number to each row in a plate and/or a series of plates, as well as the ability to achieve an even distribution of cells throughout a given well. The following procedure assures that cells are reproducibly transferred from flask to microtiter plates, and cells are evenly distributed across the surface of each well.

The first step in preparing the microtiter plates is preparing and monitoring the monolayer as described above. The following protocol is exemplary [all protocols herein are exemplary] and variations are apparent to one skilled in the art. Other methods employing microtiter plates and plating cells are publicly available, well known to those of skill in the art and are intended to be used as an option in the practice of, or in conjunction with, the assays, methods, tools and systems disclosed herein.

Cells are removed from the culture flask and a cell pellet is prepared by centrifugation. The cell pellet derived from the monolayer is then suspended in 5 ml of the growth medium and mixed in a conical tube with a vortex for 6 to 10 seconds. The tube is then rocked back and forth 10 times. A 30 µl droplet from the center of the conical tube is pipetted onto one well of a 96 well plate. A fresh pipette is then used to pipette a 30 µl aliquot of trypan blue solution, which is added to the same well, and the two droplets are mixed with repeated pipette aspiration. The resulting admixture is then divided between two hemocytometer chambers for examination using a standard light microscope. Cells are counted in two out of four hemocytometer quadrants, under 10× magnification. Only those cells which have not taken up the trypan blue dye are counted. This process is repeated for the second counting chamber. An average cell count per chamber is thus determined. Using means known in the art, the quadrant count values are checked, logged, multiplied by $10^4$ to give cells/ml, and the total amount of fluid (growth medium) necessary to suspend remaining cell aliquots is calculated accordingly.

After the desired concentration of cells in medium has been determined, the resulting cell solution is placed in a channel of a deep well plate. An automated liquid handling system delivers the appropriate amount of cell solution to each well of a 384 well microtiter plate. A plurality of plates may be prepared from a single cell suspension as needed.

After the microtiter plates have been prepared, exposure of the cells therein to one or more pharmaceutical agents is conducted according to the following exemplary protocol. During this portion of the assay, the appropriate amount of specific pharmaceutical agent or agents is transferred into the microtiter plates prepared using an automated liquid handling device.

A general protocol, which may be adapted, follows. Each microtiter plate is microscopically examined for cell adhesion. Control solution is dispensed into delineated rows of wells within the grid in the microtiter plate, and appropriate aliquots of active agent to be tested are added to the remaining wells in the remaining rows. Ordinarily, sequentially increasing concentrations of the active agent being tested are administered into progressively higher numbered rows in the plate. The plates are then incubated in a humidified incubator at 37° C. under 5% $CO_2$. After a predefined exposure time, the plates are fixed and stained for evaluation.

E. Types of Wells or Culture Plates Used

Standard tissue culture plates can be utilized for the assay comprising 384 equivalent wells. Each well is capable of holding approximately 120 µl of solution. As can be appreciated by a skilled artisan, various sizes of tissue culture plates can be used. For instance, wells may be reduced in size to hold only 80 µl. In one embodiment, the plates are made of molded plastic. Glass bottom plates of standard coverslip thickness may be used. In such a case, the glass bottom plates may be pretreated with a thin layer of extracellular matrix material such as collagen, vitrogen, fibronectin or the like.

IV. Treatment Protocols

For each drug tested as a single agent, an initial 10 dose range of concentrations to be used in the assay is determined (see below). Patient-derived tumor cells are treated with the indicated drug(s) at their indicated dosages for a period of about 25 to 200 hours. In one embodiment, the treatment period is 72 hours. However, the agent tested can dictate a shorter or longer treatment period. For instance, biological agents may require longer treatment periods than traditional pharmaceutical agents.

Beginning with Dose 10 (the highest dose tested), serial dilutions of the same magnitude are repeated to create Doses 9 through 1. Dilutions are prepared in the medium type or balanced solution that is appropriate for the tumor type and drug being tested. The initial dosages may be adjusted so that 0% cell kill is evident at Doses 1-2, and maximal cell kill is evident at Doses 9-10. Dosages are preferably validated on at least 15 patient-derived tumor cell cultures of the appropriate tumor type(s) for each drug.

Following the establishment of 25 to 200 hour dosing levels for several of the drugs tested as single agents, a new method of dealing with combination treatments was developed. The 25 to 200 hour combination drug dosing developed is consistent and flexible for numerous combinations (including 2, 3 or 4 drug combinations). Essentially the highest doses of each drug in the combination are mixed resulting in the same concentration of each drug when tested as a single agent and a serial dilution series is created to give 10 dose levels for the drugs.

A combination of immunotherapy and/or radiation treatment and/or chemotherapy is also useful for treatment of tumors that are resistant to one or more chemotherapeutic agents. Chemotherapy alone has limitations in that the cancer cells often become resistant to a broad spectrum of structurally unrelated chemotherapeutic agents. Such resistance, termed "multidrug resistance" (MDR), is not an uncommon problem in the treatment of patients with cancer and while significant efforts have been made to understand the mechanisms responsible for MDR, that understanding has not fulfilled the expectations for eradicating chemoresistant cancer cells.

Immunotherapy, alone or in combination with radiotherapy, has also been investigated as a method for inhibiting or eradicating cancer cells. Such methods are useful for treating patients whose tumors are chemoresistant to one or more chemotherapeutic agents. Immunotherapy, alone or in combination with radiotherapy, and in conjunction with the assays, methods and tools described herein are suitable for use with patients whose tumors are chemoresistant.

V. Preparation and Determination of Dose Levels

The ordinarily skilled artisan may select an appropriate amount of each individual pharmaceutical agent in the combination for use in the aforementioned assays or similar assays. Changes in chemotherapeutic drug metabolism, drug transport, cell apoptosis, cell proliferation, DNA repair or other biological activity (including gene expression) are used to determine whether the selected amounts are "effective amounts" for the particular combination of agents/compounds.

The regimen of administration also can affect what constitutes an effective amount. Further, several divided dosages, as well as staggered dosages, can be administered daily sequentially to the microtiter plates, or the dose can be proportionally increased or decreased as indicated by the exigencies of the therapeutic situation. See, for example, U.S. Pat. No. 6,599,912. In another embodiment, a first agent and a second agent are administered to the cells at the same time or in overlapping time periods; the first agent and the second agent are administered at different times; the first agent is administered first and the second agent is administered subsequently; the second agent is administered first and the first agent is administered subsequently.

Dosages of drugs are initially determined based on concentration of drug determined to be present in the extracellular fluid surrounding a tumor in vivo (information is extracted from the literature) and/or the range of concentrations of the drug reported to elicit an anticancer effect in similar in vitro models. Once use of one or more agents is indicated, the initial dosages are determined and a series of dilutions is prepared from each agent such that the range of the dilutions covers the range of initially determined doses and also includes dose levels resulting in 0% and up to and including maximal cell killing. Thus, the upper and lower levels of each agent are determined. This procedure is used on chemoresistant cells as well as cells untested for chemotherapeutic agent sensitivity.

In one embodiment of the methods and assays disclosed herein, an agent is used at a dose level where the lowest dose had a minimal effect on cell viability and the highest dose had a moderate to strong effect on cell viability. In another embodiment, the methods further include repeated dosages of the same, or a different agent. In therapeutic applications, the dosages of the agents used in the methods herein vary depending on the agent and clinical condition of the recipient patient, and the experience and judgment of the clinician or practitioner administering the therapy, among other factors affecting the selected dosage. Generally, the dose should be sufficient to result in slowing, and preferably regressing, the growth of the tumor cells and also preferably causing complete regression of the cancer in vitro or in vivo. In one embodiment, an effective amount of a pharmaceutical agent is that amount which provides an objectively identifiable slowing, or death or regression of the tumor cells in vitro. See, for example, U.S. Pat. No. 6,875,745.

In one embodiment of the assay methods included in the invention disclosed herein, the cells to be assayed are grown on microtiter plates and assayed for their sensitivity to a chemotherapeutic agent according to the above-described protocols. The microtiter plates are read on an optical scanner and data from the scanner is automatically exported to a computer for calculation of a therapeutic index. Other types of scanners may be utilized depending upon the assay. For instance, a scanner for reading RIA data would be provided if the assay is an RIA assay.

VI. Phenotypic and Genotypic Drift

It has been recognized that when patient cells are removed from their in situ locations in tissues and cultured in vitro, the cells are subject to phenotypic and genotypic drift, i.e., they begin to lose some of the morphological features (and components) of some characteristic of their tissue or organ of origin, sometimes as a result of changes in expression of a gene, or expression of a mutated gene. This instability is the result of culture condition variations, selective overgrowth of some cells in the population, and genetic variation. As it is important to standardize the culture so that the cell population remains as stable as possible over time, explants and seed stocks of the cell culture are often preserved. Cell preservation minimizes the genetic and phenotypic drift in cultures, serves to avoid senescence, guards against contamination and provides a stock culture, should the "working" culture become contaminated, change, or otherwise unusable. See, for example, U.S. Pat. No. 5,587,297 and U.S. Pat. No. 6,528,309.

In one embodiment of the invention, the adherent cells are analyzed prior to fixation and staining. Such analysis may include but is not limited to treating the remaining adherent cells with additional drugs to determine response to a second regiment of chemotherapeutic agents. Such analysis may include but is not limited to analysis of different vital stains to measure cell viability, membrane integrity, cell signaling pathways, apoptosis, multi-drug resistance (MDR) ability, etcetera. Such analysis may include but is not limited to genotypic analysis for gene expression or genome mutations, phenotype analysis, such as expression of surface proteins, cell viability, immunohistochemical analysis and pathological analysis. Subsequent to analysis of adherent cells as mentioned above, the cells are fixed and stained for counting/analysis as described in Version 2 assay method.

A. Phenotypic Changes

Changes in phenotype are monitored by a variety of ways, using techniques and methods publicly available and well known to those of skill in the art. In one aspect included in the invention, a phenotypic assay is employed to assess response to culture conditions and may also be employed to assess sensitivity and/or resistance to chemotherapeutic agents and as an indicator of the occurrence of phenotypic drift. The phenotypic assay is performed in vitro using the cultured cells. The phenotype assay also allows for identification and separation of tumor cells from other cells found in a tissue sample, as well as direct measurement and monitoring of tumor cells in response to chemotherapeutic and/or radiation treatment and/or immunotherapy treatment. Direct measurements and monitoring of live tumor cells are performed using known methods in the art including, for example, the measuring of doubling rate, proliferative assays, monitoring of cytostasis, cell death, cell adhesion, gene expression, cell motility, cell invasiveness and others. Direct measurements also include known assays, such as those directed to measurement and monitoring of apoptosis, senescence and necrosis. Phenotypic assays may also measure changes in a molecular predictor of response.

Once a primary culture and its derived secondary monolayer tissue culture have been initiated, the growth of the cells is monitored to oversee growth of the monolayer and ascertain the time to initiate the phenotypic assay. Prior to the phenotypic assay, monitoring of the growth of cells may be conducted by visual monitoring of the flasks on a periodic basis, without killing or staining the cells and without removing any cells from the culture flask. Data from periodic counting or measuring is then used to determine growth rates or cell motility, respectively, using methods known to those of skill in the art.

One embodiment of the present methods contemplates a phenotypic assay that assesses whether chemotherapeutic agents affect cell growth. Monolayer growth rate is monitored using, for example, a phase-contrast inverted microscope. Following initial culturing of the multicellular tissue explant, the tissue explant is removed from the growth medium at a predetermined time. In one embodiment of the invention, the predetermined time is 1 to 40 days after disaggregation, i.e., agitation, of the tumor specimen. In another embodiment, the predetermined time is 6 to 30 days or 6 to 28 days after disaggregation of the tumor specimen. In another embodiment, the predetermined time is 7 to 21 or 7 to 15 days after disaggregation of the tumor specimen. In yet another embodiment, the predetermined time is 7 to 10 days after disaggregation of the tumor specimen.

The predetermined time for removal of the tissue explant from growth medium can also be calculated from the time of initial culturing of the tissue explant, i.e., preparation of cell culture monolayer. In one embodiment of the invention, the predetermined time is 1 to 40 days after initial culturing of the tumor explant. In another embodiment, the predetermined time is 6 to 30 days or 6 to 28 days after initial culturing of the tumor explant. In another embodiment, the predetermined time is 7 to 21 or 7 to 15 days after initial culturing of the tumor explant. In yet another embodiment, the predetermined time is 7 to 10 days after initial culturing of the tumor explant.

In one embodiment of the methods disclosed herein, the explant is removed from the growth medium prior to the emergence of a substantial number of stromal cells from the explant. Alternatively, the explant may be removed according to the percent confluence of the cell culture. In another embodiment of the methods disclosed herein, the explant is removed at about 10 to about 50 percent confluence. In yet a different embodiment, the explant is removed at about 15 to about 25 percent confluence. In another embodiment, the explant is removed at about 20 percent confluence. By removing the explant in any of the above manners, a cell culture monolayer predominantly composed of tumor cells is produced.

In another embodiment, a phenotypic assay assesses whether chemotherapeutic agents affect cell motility. Methods for measuring cell motility are known by persons skilled in the art and any method for assessing cell motility is optionally used in conjunction with the assays and methods disclosed herein. Generally, these methods monitor and record the changes in cell position over time. Examples of such methods include, but are not limited to video microscopy, optical motility scanning (for example, see U.S. Pat. No. 6,238,874) and impedance assays. In one embodiment, cell motility assays are carried out using monolayer cultures of tumor cells as described herein.

An important aspect included in the present invention is to provide a system for screening specific tissue samples from individual patients for expressed or non-expressed cellular markers, such as receptors, secreted factors, or antigens, including tumor antigens, characteristic of the tissue sample. For instance, a tumor sample from a patient is harvested and grown in a monolayer culture as described above. Culture medium in which the cultures or subcultures thereof are assayed for the presence or absence of certain factors, such as secreted tumor antigens. These factors may be detected through use of standard assays, such as radioimmunoassay (RIA) or enzyme-linked immunosorbent assay (ELISA), although other assays known to those skilled in the art may be used to detect and/or to quantify the soluble factors.

The cell cultures grown in this manner may also be assayed histochemically and/or immunohistochemically for identification or quantification of cellular or membrane-bound markers. Examples of such markers include, without limitation, CEA, and at least one molecular predictor of response as described herein. By screening tumor samples in this manner, for production of such factors, markers or antigens, the cultured cells may be further identified and monitored, aiding the physician in treatment strategies and as a prognosis indicator. Furthermore, by combining the use of the culture technique with assaying for markers, factors or antigens as described herein, a treatment strategy for a cancer or disease state may be optimized and treatment progression may be monitored. High throughput phenotypic analysis of cells can be accomplished through the use of automated processes available commercially.

B. Genotypic Changes

Genomics is defined as the study of genes, their composition and their expression patterns. As such, genomic analysis encompasses genetic variability such as DNA mutations or single nucleotide polymorphisms (SNPs), as well as alterations in gene expression at the RNA level. More specifically, pharmacogenomics encompasses the effect of genetic variability on drug response. Although a relatively new practice, pharmacogenomics can be applied to patients with a variety of different disease types, such as hypertension, asthma and cancer. In the case of cancer pharmacogenomics, there are a variety of molecular factors which may influence chemoresponse, including, for example, pathways involved in drug metabolism, uptake, efflux, activation and detoxification, as well as target gene expression and DNA repair mechanisms. Thus, multiple genes play a role in response to chemotherapy, and genetic variations within drug pathway genes are often associated with clinical resistance to the drug's effects. These genetic alterations are often detected as SNPs and/or altered gene expression.

In the clinical setting, the goal of cancer pharmacogenomics is to develop a "predictor" of an individual patient's response to a given chemotherapeutic agent. The predictor is most commonly in the form of a subset (generally, less than 60) of SNPs and/or tumor expression of genes which is correlated with patient response to chemotherapy. From a bioinformatics perspective, the potential components of a predictor can be obtained in a variety of ways.

First, a "discovery" approach takes into consideration as many SNPs and/or genes in the human genome as possible. With the advent of the Human Genome Project, the discovery approach has become possible because of the availability of prefabricated microarrays which comprise over 30,000 human genes; additionally, "SNP chips" are also available.

Alternatively, a "candidate" gene approach may be taken. In this instance, specific genes are chosen based on biologically-based findings in the literature and/or scientific intuition; and the expression of these candidate genes can then be analyzed using more quantitative methods, such as RT-PCR. However, any method known in the art to quantitatively or qualitatively analyze gene expression is optionally used in the practice of the methods included in the invention.

Lastly, a "hybrid" of the previous two approaches may be utilized in which gene classes (e.g., cell cycle genes, apoptosis genes, cell proliferation genes, drug transport genes and drug metabolism genes) may be used as a starting point to identify genes with which to begin. Microarrays or RT-PCR may be used to determine the genes which are most predictive of patient response.

A genotype assay is performed to determine whether cells from a patient comprise a genetic characteristic associated with resistance to the chemotherapeutic agents. Genotype assays reveal latent resistance to chemotherapeutic agents not observed by phenotypic assays. Genotypic assays may measure characteristics, such as, for example, drug metabolism, drug transport, cell proliferation, apoptosis, DNA repair, toxic effects, cell invasiveness and extracellular matrix formation.

In addition, the assays often involve the evaluation of nucleic acids in tumor cells and/or the presence of polymorphisms (SNPs). The methods for evaluating the nucleic acids of tumor cells are many, and include without limitation, hybridization studies (e.g., Southern and northern blots), nucleic acid sequencing, fingerprinting (e.g., the analysis of restriction fragment length polymorphisms) and PCR-based protocols, which may be quantitative and/or qualitative in nature. These protocols may be performed in a traditional manner, i.e., by running the results on a gel, or by newer methods known in the art. Newer methods may involve miniaturization and multiplication of the traditional protocols and include nucleic acid micro arrays and a variety of applications that may be performed in connection with such micro arrays, for instance, DNA:DNA or DNA:RNA hybridizations and competitive hybridizations. Arrays permit the rapid analysis of a nucleic acid sample for the presence of or absence of hundreds to many tens of thousands independent nucleic acids. These independent nucleic acids may be from genes of known function or from nucleic acids of unknown function, i.e., expressed sequence tags (EST).

The nucleic acid can be any nucleic acid that is present in the proliferating cells, i.e., RNA or DNA. The analyzing step typically involves use of one or more analytical methods known to have the capacity to characterize the nucleic acids, including, without limitation quantitative methods that identify the amount of specific RNAs in a cell as well as qualitative methods that determines the presence of or absence of specific genetic markers, such as DNA or RNA sequence insertions, deletions or substitutions.

The data generated by the analytical process of the present invention (hereinafter, the "genetic data") can be gathered to form a record that is part of a data set in a data structure. Data indicating the phenotype of the tumor cells also may be included. This phenotypic data includes, without limitation, histochemical, immunohistochemical, biochemical and growth characteristics of the cells and/or tumor, including the production of secreted compounds, whether or not the tumor cells were cultured according to the methods of the present invention. Non-genetic analysis, i.e., phenotypic analysis, is also of value in the diagnosis of tumor diseases. The resultant non-genetic data can be combined with the above described genetic data to provide a complete and accurate profile of the tumor cells of the tissue sample.

Once a primary culture is established from a patient's abnormal proliferating cells, the primary culture can be maintained without any treatments beside normal feedings and passage techniques, as indicative of the growth of the cells absent treatment with a therapeutic regimen. Subcultures of the primary culture are prepared so that the cells of the primary culture are not affected by any subsequent testing or treatments. Although the primary culture is preferably left untreated, either the primary culture or a subculture thereof can be propagated as a reference culture. The reference culture is a culture which is treated with therapies reflective of a patient's actual treatment regimen. For instance, if a patient is treated with a chemotherapeutic agent, the reference culture is treated with the same agent in the same concentration. The reference culture can be monitored genotypically and/or phenotypically to reflect actual progress of the tumor or disease or condition in the patient. Treatment of the reference culture need not be limited to anticancer therapies, but can reflect all of a patient's treatments. For instance, thrombolytic or antithrombogenic treatments can be applied to the reference culture to reflect a patient's treatment and to indicate a possible interaction of other drugs with the chemotherapeutic agent(s). Subcultures of either the primary culture or the reference culture can be used for further analysis, such as the genotypic analysis or phenotypic analysis techniques of the present invention. Preferably, since the reference culture is indicative of the current state in a patient of a tumor or disease, subcultures of the reference culture are analyzed.

Molecular predictors of response may be monitored by genotypic assays, phenotypic assays or both using patient tumor cells obtained or cultured by one or more of the methods disclosed herein at any stage of the culture process. The cells to be monitored include untested tumor cells, known chemoresistant tumor cells and known chemosensitive tumor cells.

At various points in the passage of the control culture and the reference culture, aliquots of cells from those cultures can be stored cryogenically or otherwise. Tumor cells prepared according to the culture methods of the present invention are then genetically analyzed for markers specific to the tumor or disease state of the cells. The cells that are analyzed typically are from subcultures of the primary or reference cultures. In this process, nucleic acid is isolated from the cells and is analyzed to identify markers that are characteristic of abnormal proliferating cells. The isolated nucleic acid is DNA or RNA. The nucleic acid, preferably, is analyzed in a microarray for expression of one or more genes.

Preferably, the microarray contains nucleic acids that are characteristic of known proliferative or tumor disease states, as well as nucleic acids, that are not correlated with known proliferative or tumor disease states, so that previously unknown relationships between gene expression and a cancer, proliferative disease or condition may be identified. Methods for isolation and analysis of the nucleic acids of the cells are varied and typically differ from laboratory to laboratory. Further, certain analytical methods may require that the nucleic acid is prepared in a specific manner. Nucleic acid purification methods may be found in anyone of a number of molecular biology laboratory texts. Purification products or systems also are commercially available.

The presence of known proliferation markers, such as the expression of one or more genes, may be determined by methodologies, without limitation, by northern blotting or quantitative polymerase chain reaction (PCR) methods, i.e., RT-PCR.

Microarrays of either known DNAs or unknown DNAs, i.e., partially identified or unidentified expressed sequence tags (ESTs), are now commercially available from a large number of commercial sources. Custom microarrays may be prepared in the laboratory with commercially available robotic devices or can be purchased from one or more commercial sources for microarrays. DNA microarrays can include hundreds to many thousands of unique DNA samples covalently bound to a glass slide or other substrate in a very small area. By hybridizing labeled cDNA or other labeled nucleic acid or ligand that can be hybridized specifically to the covalently-bound nucleic acid to the array, the altered expression of one or more genes may be identified.

It is possible to label cDNA from two cell types, i.e., normal and tumor cells, and hybridize equivalent amounts of both probe populations to a single microarray to identify differences in RNA expression for both normal and tumor cells. Tools for automating preparation and analysis of micro array assays, such as micro array scanners and readers, are available commercially. The automation of the microarray analytical process is desirable and, for all practical purposes necessary, due to the huge number and small size of discrete sites on the micro array that must be analyzed.

DNA microarrays are possibly the more powerful tools to utilize in combination with the cell culturing method of the present invention due to the increased sensitivity of mRNA quantification protocols when a substantially pure population of tumor cells is used. For their ease of use and their ability to generate large amounts of data, microarrays are preferred, when practicable. However, certain other or additional qualitative assays may be preferred in order to identify certain markers.

The presence of, or absence of, specific RNA or DNA species also may be identified by PCR procedures. Known genetic polymorphisms (SNPs), translocations, or insertions (e.g., retroviral insertions or the insertion of mobile elements, such as transposons) often can be identified by conducting PCR reactions with DNA isolated from cells cultured by the methods of the present invention.

Where the sequence anomalies are located in exons, the genetic polymorphisms may be identified by conducting a PCR reaction using a cDNA template. Aberrant splicing of RNA precursors also may be identified by conducting a PCR reaction using a cDNA template. An expressed translocated sequence may be identified in a microarray assay. Small or single nucleotide substitutions may be identified by the direct sequencing of a given gene by the use of gene-specific oligonucleotides as sequencing primers. Single nucleotide mutations also may be identified through the use of allelic discrimination molecular beacon probes. See, for example, those described in Tyagi, S. and Kramer, F. R. (1996) *Nature Biotech.* 14:303-308 and in Tyagi, S. et al., (1998) *Nature Biotech.* 16:49-53. Mass spectrometry (MALDI-TOF) may also be used to identify mutations.

While the above-mentioned assays are useful in the analysis of nucleic acids derived from cells produced by the culture methods included in the invention, numerous additional methods are known in the general fields of molecular biology and molecular diagnostics that may be used in place of the above-referenced methods.

Any or all of the steps of the unified assays and culturing techniques included in the present invention may be automated. Data can be input into the computer either manually or automatically, into a spreadsheet or database program, or the like. The spreadsheet or database program can be programmed to reduce the data to the indices described above, or to any other relevant form, i.e., graphical or figurative representations of the data.

The methods of the invention further include the step of characterizing the tumor cells by analyzing the genetic and/or phenotypic data in connection with a set of corresponding clinical data for statistically significant commonalities and/or trends to generate one or more profiles which link one or more proliferative cell disease states with phenotypic and/or genotypic characterizations, diagnoses and/or prognoses. These data and/or profiles may be encoded in a computer storage medium and stored in a data base. The contents of these databases include, but are not limited to, observed in vitro phenotypes (disease factors) and genotypes (host factors). A method for diagnosing proliferative diseases is also provided that compares either 1) the genetic and corresponding clinical data and/or 2) the profiles generated therefrom, to data generated in connection with a new tissue sample. By applying analytical techniques to the stored phenotypic and genotypic information, predictions of chemotherapeutic efficacy can be made. A computer system containing the data and/or profiles is also provided that, optionally, allows dissemination and/or analysis of the data over a computer network.

VII. Method of Generating a Dose Response Curve

Cells harvested from patient tumor explants can be seeded into a black-walled, clear bottom 384 microplate at a concentration of about 4,000 to 12,000 cells/ml and 30-50 µl of cell suspension per well. In one embodiment, explants are seeded at a concentration of about 8,000 cells/ml and 40 µl of cell suspension per well. Cells can be seeded according to the number of drug treatments requested by the oncologist with three replicates per dose of each drug. To prevent evaporation of medium, the outermost ring of wells on the microplate can be filled with buffer, for instance, about 80 µl of Hank's Balanced Salt Solution (HBSS). Cells can then be allowed to attach to the bottom of the microplate during a 24 hour incubation period. After the initial incubation, doses of each drug, or combination of drugs, can be added to the patient plate with about 30 to 50 µl of a dose per well and one control well treated with growth medium per 10 doses.

In one embodiment, immediately prior to drug application, images of the cells are taken with an automated cell imaging system using visible light. The microtiter plate is placed on the automated cell imaging system. Each well of a microtiter plate is scanned to capture images. Alternatively, only previously selected wells are imaged. Images are analyzed to determine the number of cells in each well. Then each well is treated with the appropriate amount of drug, and the cells are incubated with drug for a set about of time. In one embodiment, the cells are incubated with drug for about 25-200 hours. At about a specified time after plating, for instance, at about 96 hours after plating, the cells are again imaged with visible, fluorescent and UV light using the automated cell imaging system. Cellular imaging after 96 hours can be accomplished by visible light or through fluorescent light utilizing the appropriate cellular fluorescent dyes. Such fluorescent dyes may label the nucleus, the cell membrane, organelles, or constituents of the cytoplasm. Alternatively, the fluorescent dye may require activation in metabolically active cells, in which case only living cells would fluoresce. The wavelengths of fluorescent light range from 250 nm to 800 nm depending on the characteristics of the fluorescent dye. Using an automated imaging system to capture images enables the unique identification of each cell or cell confluency based on visible imaging or fluorescent light in each well.

The cells can then be fixed in the plate using ethanol or other standard fixative used in the art and stained with a nuclear stain, such as DAPI. The automated cell imaging system can then be used to take fluorescent images of the patient cells so that cell nuclei can be counted. The data generated from the visible and fluorescent images can then be used to generate dose response curves for each drug the patient cells were treated with.

In one embodiment of the method, prior to fixation of the cells, the cells are treated with two fluorescent dyes which are able to distinguish living from dead cells. The integrity of the stains survives the fixation process. After fixation, the cells are stained with a nuclear stain, such as DAPI. The automated imaging system can then capture images with three different wavelengths of light. Subsequent analysis of the images can enable the determination for each cell of a live or dead status. The data generated from the visible and fluorescent images can then be used to generate dose response curves for each drug the patient cells were treated with.

VIII. Methods of Cell Fixing and Staining

Fixing and staining may be conducted according to a number of suitable procedures; the following is representative. Other methods of fixing and staining cells are publicly available, well known to those of skill in the art and are intended to be used as an option in the practice of the methods disclosed herein.

For example, when fluorescent light is used to quantitate cells (e.g., to determine viability or confluence), a stain such as calcein AM or a cytotracker dye can be used. Fluorescent images can be taken of the cells at predetermined intervals or at any time throughout the course of the experiment to track the cell counts (for example, viability due to the effects of the one or more agents on confluence). The dyes chosen for this procedure should not affect either cell growth characteristics or drug efficacy characteristics.

In one embodiment of the invention, after removal of the plates from the incubator box, culture medium/drug is removed by an automated liquid handler. Continuing to use the automated liquid handler, the plates are rinsed with about 40-60 µl of HBSS, and about 40-80 µl of ethanol is added to each well of the plate for at least 10 minutes. Ethanol is removed, and staining is accomplished with approximately about 50-70 µl of a DAPI solution per well for at least 20 minutes. The automated liquid handler removes the DAPI solution from each well, followed by the addition of about 50-70 µl of water. The plates are now prepared to be scanned.

Alternatively, this procedure may be performed manually, in the absence of an automated liquid handler. In that instance, plates are removed from the incubator and culture medium/drug is removed from each well with a manually operated pipette. 60-80 µl of ethanol is added to each well for at least 10 minutes. Ethanol is removed by plate inversion and vigorous shaking. 60-80 µl of DAPI solution is added to each well for at least 20 minutes, followed by removal via plate inversion and vigorous shaking. After about 60-80 µl of water is added to each well, the plates can be scanned.

Cells per well are then counted manually or by automated and/or computerized means, to derive data regarding chemosensitivity of cells at various concentrations of exposure. One particularly useful computer operating environment for counting cells is the commercially available OPTI-MATE compiler, which is designed to permit an optical counting function well suited to computerized cell counting procedures and subsequent calculations. Other techniques for counting cells are publicly available, well known to those of skill in the art, and intended to be used as an option in the practice of the methods disclosed herein.

The techniques disclosed herein for fixing and counting cells is intended as exemplary; other methods are known in the art and intended to be used as an option in the practice of the methods disclosed herein. The same cell culturing and well distribution process is used as in the cytotoxicity assay described above, but rather than exposing the cells to chemotherapeutic or other agents, the cells are instead fixed and stained. With the stain or stain cocktail described below, the epithelial cells are identified by their intermediate filaments and/or specific membrane antigens by means of a monoclonal antibody immunoperoxidase technique. The fixative used can be any fixative which does not alter the cellular markers of interest. The fixed, stained cells are then counted. If the specimen is positive for epithelial cells, the process is complete. If the specimen is negative for epithelial cells, an independent fixing and staining process is subsequently completed, with fresh cells from identical wells, using Vimentin or other non-epithelial cell markers as a stain to confirm the non-epithelial nature of the cells.

The importance of having a stain or stain cocktail (for example, a cocktail comprised of at least one antibody), as well as an overall protocol, for identifying epithelial cells in explants or biopsies of malignant tumors is as follows. In the basic cytotoxicity assay, the tissue culture technique is designed to grow out the cells of the tumor of origin and in fact consistently does so. Despite such reliable predictability, however, the fact that the cells of the tumor of origin did in fact grow out, and not fibroblasts or other cells, can be confirmed with independent proof before the cells are used with complete assurance in the appropriate patient assay(s). The present technology provides a means to obtain this confirmation, which in turn furthers the interests of good laboratory and medical practice.

In general, the staining compounds or compositions of interest for use in the present technology are those which bind with cellular molecular markers unique either to epithelial or to non-epithelial cells. The methods disclosed herein improve the cytotoxicity assay by adding the epithelial staining protocol with any known epithelial stain and a further improvement wherein specially designed stain cocktails maximize the likelihood that the presence of any known intermediate filament or specific membrane antigen, characteristic of epithelial cells, will be identified if present.

Many carcinomas are positive for any one of the intermediate filaments or specific membrane antigens characteristic of epithelial cells; virtually all if not all carcinomas are positive for one of a number of such intermediate filaments or specific membrane antigens. For example, "epithelial membrane antigen" (EMA) glycoproteins are known in the art and can be bound with various antiepithelial membrane antigen antibodies including monoclonal antibodies. Cytokeratin is another important epithelial cell marker and binding reagents including monoclonal antibodies are available which are specific to cytokeratin. While antisera can be raised in vivo against markers such as EMA glycoproteins and cytokeratin, as a practical matter commercially available polyclonal or monoclonal antibodies are used in the following protocols, with monoclonal antibodies being preferred.

IX. Targeting Agents

Binding of the targeting agent to the epithelial marker is revealed with associated staining procedures and reactions which give a visual indication that the marker binding took place. Various techniques already available to reveal whether marker binding took place. One known way to accomplish this visualization when antibody binding reagents are used is with the "labeled streptavidin procedure." In this procedure, after the specimen is exposed to antibodies specific to the target antigen, a secondary "link" antibody is added. The secondary biotinylated "link" antibody consists of anti-mouse and anti-rabbit antibodies which bind universally to most primary monoclonal or polyclonal antibodies. The "link" will also connect to the tertiary reagent (peroxidase-labeled streptavidin) through chemical bonding between the biotin on the secondary reagent and the streptavidin on the streptavidin/peroxidase conjugate. Staining is completed by incubating the specimen and primary, secondary and tertiary agents in the presence of a chromogen, so that the peroxidase and the chromogen form a visible precipitate. Alternatively, a fluorescein-based detection system can be used to visualize the primary antibody, or a third alternative known in the art as the digoxigenin-conjugated detection system may be used.

There is an advantage in using one or more binding reagents together. The combination of two general binding reagents (containing a total of three monoclonal antibodies) for cytokeratin, for example, admixed with a general binding reagent for EMA glycoprotein, for example, is advantageous. The dual benefit of this admixture of general binding agents is that the incidence of false negatives for epithelial cells is minimized, and the visible staining reactions are generally stronger when the combined binding reagents are used in lieu of a single binding reagent.

Although the binding reagents and other reagents identified in the Examples are the preferred reagents for use in the practice of the methods disclosed herein, the invention is intended to encompass epithelial-specific binding and staining reagents generally. These include, without limitation: Boehringer-Mannheim AE1 anti-cytokeratin antibody; Boehringer-Mannheim AE3 anti-cytokeratin antibody; Boehringer-Mannheim AE1/AE3 anti-cytokeratin antibody (AE1 and AE3 in admixture); Becton-Dickinson CAM 5.2 antibody, DAKO EMA antibody, Biomeda's Anti-Cytokeratin Cocktail CK22, Biomeda's Anti-Cytokeratin Cocktail CK23, Biomeda's Anti-Pan-Cytokeratin CK56, Biomeda's polyclonal goat or rabbit anti-cytokeratin antisera, ScyTek Laboratories' anti-EMA antigen antibody clone E29, and many others. Those skilled in the art and in possession of the guidance provided herein can readily determine alternative, equivalent binding and staining reagents and cocktails, to accomplish the disclosed result. These binding agents and cocktails may be used in combination with any known visualization system, such as the streptavidin, fluorescein- and digoxigenin-conjugated systems identified above. As a control, Vimentin antibody is used as a binding alternative either in conjunction with binding and staining of the test cells, or subsequently thereto. Vimentin can be considered a binding reagent which is specific to non-epithelial cells of mesenchymal origin.

In a further aspect of the present methods, immunological markers may be monitored in applications requiring up- or down-regulation of such markers, such as, for example, Major Histocompatibility Complex (MHC) molecules. This aspect can be especially useful in monitoring phenotypic or genotypic drift.

X. Pharmaceutical Agents

In conventional therapy, residual tumor cells are left undamaged due to chemoresistance or due to the fact that these cells are located in hypoxic areas poorly vascularized and not accessible to conventional treatments. The genetic instability and heterogeneity of tumors allows them to adapt and to develop resistance to therapies. The beneficial effects of chemotherapy can be compromised by cellular mechanisms that allow tumor tissue to evade the toxicity of drugs. In some cases, pleiotropic resistance to a variety of unrelated drugs has been observed, and this phenomenon has been called multidrug resistance. To combat multidrug resistance and to increase efficacy of treatment, therapies comprised of one or more agents (combination therapies) have been developed.

A combination therapy includes one or more of the following chemotherapeutic agents: anthracyclins, daunorubicin, adriamycin, taxoid derivatives, vinca alcaloids, vincristine, carmustine, cisplatin, fluorouracils, cytostatic compounds such as polyamine inhibitors, topoisomerase inhibitors, tamoxifene, prodasone, or sandostatine, or compounds inducing apoptosis such as sodium butyrate or mitomycin C, protease inhibitors or foscarnet. An agent in the combination therapy may also be an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway, a selective estrogen receptor modulator, an aromatase inhibitor, an agent that promotes apoptosis and/or necrosis, an interferon, an interleukin, a tumor necrosis factor, and radiation. In one embodiment of the methods disclosed herein, the agent is one or more of paclitaxel, interferon alpha, gemcitabine, fludarabine, carboplatin, cisplatin, doxorubicin, epirubicin, 5-fluorouracil, leucovorin, UFT, tamoxifen, goserelin, ketoconazole, leuprolide (Lupron) or flutamide. In one embodiment, an agent is vinblastine, vincristine, vindesine, vinorelbine, docetaxel (e.g., Taxotere), camptothecin, topotecan, irinotecan hydrochloride (e.g., Camptosar), etoposide, mitoxantrone, daunorubicin, idarubicin, teniposide, amsacrine, merbarone, piroxantrone hydrochloride, methotrexate, 6-mercaptopurine, 6-thioguanine, fludarabine phosphate, cytarabine (Ara-C), trimetrexate, acivicin, alanosine, pyrazofurin, N-Phosphoracetyl-L-Aspartate, Phosphoracetyl-L-Asparate (PALA), pentostatin, N-Phosphoracetyl-L-Asparate, pentostatin, 5-azacitidine, 5-azacitidine, 5-Aza-5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, oxaliplatin, mitomycin C, melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, tamoxifen, 4'-cyano-3-(4-(e.g., Zoladex) and 4'-cyano-3-(4-fluorophenylsulphonyl)-2-hydroxy-3-methyl-3'-(trifluoromethyl)propionanilide, pemetrexed and radiation. In one embodiment, an agent is the biologically active metabolite of any of the above listed agents.

Biological response modifiers may also be used. Such agents include for example, anti-Her2/neu antibodies (e.g., Herceptin), anti-EGFR antibodies (e.g., Erbitux), other growth factor receptor antibodies (e.g., Avastin), small molecule inhibitors (e.g., Tarceva, Iressa), anti-CD20 (e.g., Rituxan), interferon alpha, interferon beta, interferon gamma, interleukin 2, interleukin 4, interleukin 12 and tumor necrosis factors.

The agents described here may be used in the cell culture methods singly or in a cocktail containing two or more agents or one of the agents with other therapeutic agents, including but not limited to, immunosuppressive agents, potentiators and side-effect relieving agents.

The therapeutic agents may be compositions also including, depending on the formulation desired, pharmaceutically-acceptable, nontoxic carriers or diluents. Many pharmaceutically acceptable carriers are known in the art (See, for example, Remington's Pharmaceutical Sciences) and are optionally used in the practice of any of the methods or assays of the invention. The diluent is selected so as not to affect the biological activity of the combination. Examples of such diluents are distilled water, physiological saline, Ringer's solution, dextrose solution, and Hank's balanced salt solution. In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, or desired chemoresponse.

XI. Apoptosis Assay

It is now well documented that the induction of apoptosis in tumor cells is a key mechanism for most anti-tumor therapies, including chemotherapy, radiation, immunotherapy and cytokines. More recently, studies have applied measurement of the apoptotic response to the determination of chemosensitivity. These studies indicate that drug-induced apoptosis but not antiproliferative measurement, can predict tumor response to chemotherapeutic drugs. Furthermore, the in vitro response of tumor cells exposed to physiological doses of chemotherapeutic agents can be tested for sensitivity or resistance by employing markers of apoptosis which correlate with tumor cell death. Methods of inducing, measuring and monitoring apoptosis are known in the art (See, for example, International Appl. No. PCT/US04/039650) and are optionally used in conjunction with the assays, methods, tool and systems included in the invention disclosed herein.

XII. Choice of Agent(s)

In one aspect included in the invention, a course of chemotherapy is selected based on results obtained from the chemosensitivity, phenotypic, genotypic and/or apoptosis assays. The present invention includes the assessment of the likelihood of whether chemotherapeutic agents will be effective in treating a malignancy in a patient. Assessment of results from phenotypic assays optionally in combination with genotypic assays optionally in combination with apoptosis assays, as well as assessment of at least one molecular predictor of response, operates to minimize the risk of administering to a patient a chemotherapeutic agent or combinations of chemotherapeutic agents to which the tumor is resistant. In one aspect of the invention, chemotherapeutic agents or combinations of chemotherapeutic agents are selected for treatment where an effect on cellular phenotype is observed and the genotypic characteristics associated with resistance are not observed. In another aspect of the invention, chemotherapeutic agents or combinations of chemotherapeutic agents are selected for treatment where an effect on cellular phenotype is not observed and the genotypic characteristics associated with resistance are observed. In a different aspect of the invention, chemotherapeutic agents or combinations of chemotherapeutic agents are selected for treatment where an effect on both cellular phenotype and cellular genotype is observed or is not observed.

XIII. Molecular Predictors of Response

As used herein, a molecular predictor of response is the expression of, or expression product of, one or more genes in one or more biochemical pathway. Nearly 60 genes have been identified whose expression and/or related SNPs are believed to play a role in response to chemotherapy. This candidate gene list includes genes involved in chemotherapeutic drug metabolism (for example, YP3A4, CYP3A5, CYP2D6, CYP2C8 and CYP2C9), drug transport (for example, ABCB1, ABCC2 and ABCG2), cell apoptosis (for example, BCL2, BAD, BAX and BAKI), cell proliferation (for example, EGRI, CYR61, p21/WAF and TP53), and DNA repair (for example, RCC1, ERCC2, MLH1 and MSH2). Molecular predictors used are selected from the group consisting of: ABCB1; ABCC1; ABCC2; ABCG2; ABL1; ACLY; ADH1A; ADPRT; ADSS; AKAP2; AKT1; AKT2; ALDH1A1; ALDH4; ANK3; ANXA8; AP2B1; APAF-1; APH-1A; AP15; APOE; ATF5; ATP7B; B4-2; BAD; BAG1; BAK1; BARX2; BAX; BBC3; BCL2; BCL2L1; BCL2L2; BNIP3; BRCA1; BRCA2; BRF2; BTF3; BUB1; BUB3; C8orf2; CASP2; CBR1; CCNL2; CCNB1; CCNE2; CD44; CD68; CDA; CDC45L; CDK9; CEACAM6; CEGP1; CENPA; CES1; CFFM4; CFLAR; COL1A1; COL4A2; COX17; CPR2; CREM; CSNK2B; CTSL2; CUL1; CYP1B1; CYP2A6; CYP2B6; CYP2C8; CYP2C9; CYP2C19; CYP2D6; CYP3A4; CYP3A5; CYR61; DC13; DCK; DCTD; DD96; DDB1; DIA4; DLC1; DNAJD1; DPYD; DPYS; ECGF1; ECT2; EFEMP1; EGR1; EMP-1; EPB42; EPRS; ER; ERBB2; ERCC1; ERCC2; ERCC4; ERG; ESM1; EXT1; FAAH; FCGRT; FDXR; FGF18; FGFR2; FLJ10948; FLJ11190; FLJ11196; FLJ13855; FLJ14299; FLJ20323; FLJ20585; FLNA; FLT1; FN 1; GADD34; GADD153; GBX2; GJB1; GNAZ; GMPS; GRB7; GSR; GSTM1; GSTM3; GSTP1; GTF2H3; HBOA; HCFC1; HEC; HER2; HLA-C; HMG1; HN1; HSPC134; IGFBP5; IL4R; ISGF3G; ITGA5; Ki67; KIAA0175; KIAA0281; KIAA0303; KIAA1041; KIAA1067; KIAA1442; KIP2; KIT; KLK4; KNTC2; KPNA2; KRT13; L2DTL; LAMB1; LCHN; LDHA; LOC51061; LOX; MAD2L1; MAP2K4; MAP4; MAPT; MCM2; MCM6; MGMT; MGST1; MLH1; MMP9; MMP11; MP1; MPO; MSH2; MSN; MUC1; MYBL2; MYC; NDP; NFAT5; NFATC3; NFKB1; NME1; NME2; NMT1; NMU; NPM 1; NR1I2; ORC6L; ORM1/2; OXCT; p21/WAF; PAPPA; PB1; PCDHB2; PCSK7; PEC1; PGK1; PGR; PK428; PLD3; POLA2; POLB; POLE; POLH; POR; PP591; PPP2R1A; PRC1; PRKDC; PRPSAP1; PSME 1; PTK2; PTPRC; RAB6B; RAB11FIP1; RALGDS; RFC4; RNF2; RPL27; RRM1; RRM2; RTKN; SCARA3; SCUBE2; SEC61A1; SERF1A; SIAH2; SLC2A3; SLC7A10; SLC28A1; SLC28A2; SLC29A1; SLC29A2; SLC35B1; SM20; SOD1; SPARC; STK15; STOML1; SURF4; SURVIVIN; TBPL1; TCEB3; TDP1; TFRC; TGFB3; TIMP1; TIMP3; TLOC1; TNC; TNF; TNFSF6; TOP1; TOP2A; TP53; TRAG3; TUBB/TUBA2; TWIST; TXN; TYMS; UBE2M; UBCH10; UBPH; UCH37; UMP-CMPK; UMPS; UP; UPB1; USP22; WISP 1; XIAP; XIST; XPA; XPB and XRCC1. The GenBank Accession number for each gene or gene fragment is provided in Table 1. All the accession numbers are incorporated herein by reference.

TABLE 1

Genes and GenBank Accession Numbers

| Gene | Accession No. |
|---|---|
| ABCB1 | NM_000927 |
| ABCC1 | NM_004996, NM_019862, NM_019898, NM_019899, NM_019900, NM_019901, NM_019902 |
| ABCC2 | NM_000392 |
| ABCG2 | NM_004827 |
| ABL1 | NM_005157, NM_007313 |
| ACLY | NM_001096, NM_198830 |
| ADH1A | NM_000667 |
| ADPRT | NM_001618 |
| ADSS | NM_001126 |
| AKAP2 | NM_001004065 |
| AKT1 | NM_001014431, NM_001014432, NM_005163 |
| AKT2 | NM_001626 |
| ALDH1A1 | NM_000689 |
| ALDH4 | NM_003748, NM_170726 |
| ANK3 | NM_001149, NM_020987 |
| ANXA8 | NM_001630 |
| AP2B1 | NM_001030006, NM_001282 |
| APAF-1 | NM_001160, NM_013229, NM_181861, NM_181868, NM_181869 |
| APH-1A | NM_016022 |
| AP15 | NM_006595 |
| APOE | NM_000041 |
| ATF5 | NM_012068 |
| ATP7B | NM_000053, NM_001005918 |
| B4-2 | NM_006813 |
| BAD | NM_004322, NM_032989 |

TABLE 1-continued

Genes and GenBank Accession Numbers

| Gene | Accession No. |
|---|---|
| BAG1 | NM_004323 |
| BAK1 | NM_001188 |
| BARX2 | NM_003658 |
| BAX | NM_004324 |
| BBC3 | NM_014417 |
| BCL2 | NM_000633, NM_000657 |
| BCL2L1 | NM_001191, NM_138578 |
| BCL2L2 | NM_004050 |
| BNIP3 | NM_004052 |
| BRCA1 | NM_007294, NM_007295, NM_007296, NM_007297, NM_007298, NM_007299, NM_007300, NM_007301, NM_007302, NM_007303, NM_007304, NM_007305, NM_007306 |
| BRCA2 | NM_007296 |
| BRF2 | NM_018310 |
| BTF3 | NM_001207 |
| BUB1 | NM_004336 |
| BUB3 | NM_001007793, NM_004725 |
| C8orf2 | NM_001003790, NM_001003791, NM_007175 |
| CASP2 | NM_001224, NM_032982, NM_032983 |
| CBR1 | NM_001757 |
| CCNL2 | NM_030937 |
| CCNB1 | NM_031966 |
| GCNE2 | NM_004702, NM_057735, NM_057749 |
| CD44 | NM_000610, NM_001001389, NM_001001390, NM_001001391, NM_001001392 |
| CD68 | NM_001251 |
| CDA | NM_001785 |
| CDC45L | NM_003504 |
| CDK9 | NM_001261 |
| CEACAM6 | NM_002483 |
| CEGP1 | NM_020974 |
| CENPA | NM_001809 |
| CES1 | NM_001025194, NM_001025195, NM_001266 |
| CFFM4 | NM_021201, NM_206938, NM_206939, NM_206940 |
| CFLAR | NM_003879 |
| COL1A1 | NM_000088 |
| COL4A2 | NM_001846 |
| COX17 | NM_005694 |
| CPR2 | NM_004749, NM_030900, NM_199122 |
| CREM | NM_001881, NM_181571, NM_182717, NM_182718, NM_182719, NM_182720, NM_182721, NM_182722, NM_182723, NM_182724, NM_182725, NM_182769, NM_182770, NM_182771, NM_182772, NM_182850, NM_182853, NM_183011, NM_183012, NM_183013, NM_183060 |
| CSNK2B | NM_001333 |
| CTSL2 | NM_001333 |
| CUL1 | NM_003592 |
| CYP1B1 | NM_000104 |
| CYP2A6 | NM_000762 |
| CYP2B6 | NM_000767 |
| CYP2C8 | NM_000770, NM_030878 |
| CYP2C9 | NM_000771 |
| CYP2C19 | NM_000769 |
| CYP2D6 | NM_000106, NM_001025161 |
| CYP3A4 | NM_017460 |
| CYP3A5 | NM_000777 |
| CYR61 | NM_001554 |
| DC13 | NM_020188 |
| DCK | NM_000788 |
| DCTD | NM_001012732, NM_001921 |
| DD96 | NM_005764 |
| DDB1 | NM_001923 |
| DIA4 | NM_000903, NM_001025433, NM_001025434 |
| DLC1 | NM_006094, NM_024767 |
| DNAJD1 | NM_013238 |
| DPYD | NM_000110 |
| DPYS | NM_001385 |
| ECGF1 | NM_001953 |
| ECT2 | NM_018098 |
| EFEMP1 | NM_004105, NM_018894 |
| EGR1 | NM_001964 |
| EMP-1 | NM_001423 |
| EPB42 | NM_000119 |
| EPRS | NM_004446 |
| ER | NM_000125 |
| ERBB2 | NM_001005862, NM_004448 |
| ERCC1 | NM_001983, NM_202001 |
| ERCC2 | NM_000400 |
| ERCC4 | NM_005236 |
| ERG | NM_004449, NM_182918 |
| ESM1 | NM_007036 |
| EXT1 | NM_000127 |
| FAAH | NM_001441 |
| FCGRT | NM_004107 |
| FDXR | NM_004110, NM_024417 |
| FGF18 | NM_003862, NM_033649 |
| FGFR2 | NM_000141, NM_022969, NM_022970, NM_022971, NM_022972, NM_022973, NM_022974, NM_022975, NM_022976, NM_023028, NM_023029, NM_023030, NM_023031 |
| FLJ10948 | NM_018281 |
| FLJ11190 | NM_018354 |
| FLJ11196 | NM_018357, NM_197958 |
| FLJ 13855 | NM_023079 |
| FLJ14299 | NM_025069 |
| FLJ20323 | NM_019005 |
| FLJ20585 | XM_371575, XP_371575 |
| FLNA | NM_001456 |
| FLT1 | NM_002019 |
| FN 1 | NM_002026, NM_054034, NM_212474, NM_212475, NM_212476, NM_212478, NM_212482 |
| GADD34 | NM_014330 |
| GADD153 | NM_004083 |
| GBX2 | NM_001485 |
| GJB1 | NM_000166 |
| GNAZ | NM_002073 |
| GMPS | NM_003875 |
| GRB7 | NM_001030002, NM_005310 |
| GSR | NM_000637 |
| GSTM1 | NM_000561 |
| GSTM3 | NM_000849 |
| GSTP1 | NM_000852 |
| GTF2H3 | NM_001516 |
| HBOA | NM_007067 |
| HCFC1 | NM_005334 |
| HEC | NM_006101 |
| HER2 | NM_001005862, NM_004448 |
| HLA-C | NM_002117 |
| HMG1 | NM_002128 |
| HN1 | NM_001002032, NM_001002033, NM_016185 |
| HSPC134 | NM_014169 |
| IGFBP5 | NM_000599 |
| IL4R | NM_000418, NM_001008699 |
| ISGF3G | NM_006084 |
| ITGA5 | NM_002205 |
| Ki67 | NM_002417 |
| KIAA0175 | NM_014791 |
| KIAA0281 | NM_014800, NM_130442 |
| KIAA0303 | XM_291141 XP_291141 |
| KIAA1041 | NM_014947 |
| KIAA1067 | NM_001013839, NM_015219 |
| KIAA1442 | XM_044921 XP_044921 |
| KIP2 | NM_000076 |
| KIT | NM_000222 |
| KLK4 | NM_004917 |
| KNTC2 | NM_006101 |
| KPNA2 | NM_002266 |
| KRT13 | NM_002274, NM_153490 |
| L2DTL | NM_016448 |
| LAMB1 | NM_002291 |
| LCHN | AB032973, AF116707, AF136629, BC012493 |
| LDHA | NM_005566 |
| LOC51061 | NM_015914 |

TABLE 1-continued

Genes and GenBank Accession Numbers

| Gene | Accession No. |
|---|---|
| LOX | NM_002317 |
| MAD2LI | NM_002358 |
| MAP2K4 | NM_003010 |
| MAP4 | NM_002375, NM_030884, NM_030885 |
| MAPT | NM_005910, NM_016834, NM_016835, NM_016841 |
| MCM2 | NM_004526 |
| MCM6 | NM_005915 |
| MGMT | NM_002412 |
| MGST1 | NM_020300, NM_145764, NM_145791, NM_145792 |
| MLH1 | NM_000249 |
| MMP9 | NM_004994 |
| MMP11 | NM_005940 |
| MP1 | NM_021970 |
| MPO | NM_000250 |
| MSH2 | NM_000251 |
| MSN | NM_002444 |
| MUC1 | NM_001018016, NM_001018017, NM_001018021, NM_002456 |
| MYBL2 | NM_002466 |
| MYC | NM_002467 |
| NDP | NM_000266 |
| NFAT5 | NM_006599, NM_138713, NM_138714, NM_173214, NM_173215 |
| NFATC3 | NM_004555, NM_173163, NM_173164, NM_173165 |
| NFKB1 | NM_003998 |
| NME1 | NM_000269, NM_198175 |
| NME2 | NM_001018136, NM_001018137, NM_001018138, NM_001018139, NM_002512 |
| NMT1 | NM_021079 |
| NMU | NM_006681 |
| NPM 1 | NM_002520, NM_199185 |
| NR1I2 | NM_003889, NM_022002, NM_033013 |
| ORC6L | NM_014321 |
| ORM1/2 | NM_000607, NM_000608 |
| OXCT | NM_000436 |
| p21/WAF | NM_000389, NM_078467 |
| PAPPA | NM_002581 |
| PB1 | NM_018165, NM_018313, NM_181041, NM_181042 |
| PCDHB2 | NM_018936 |
| PCSK7 | NM_004716 |
| PECI | NM_006117, NM_206836 |
| PGK1 | NM_000291 |
| PGR | NM_000926 |
| PK428 | NM_003607 |
| PLD3 | NM_001031696, NM_012268 |
| POLA2 | NM_002689 |
| POLB | NM_002690 |
| POLE | NM_006231 |
| POLH | NM_006502 |
| POR | NM_000941 |
| PP591 | NM_025207, NM_201398 |
| PPP2R1A | NM_014225 |
| PRC1 | NM_003981, NM_199413, NM_199414 |
| PRKDC | NM_006904 |
| PRPSAP1 | NM_002766 |
| PSME 1 | NM_006263, NM_176783 |
| PTK2 | NM_005607, NM_153831 |
| PTPRC | NM_002838, NM_080921, NM_080922, NM_080923 |
| RAB6B | NM_016577 |
| RAB11FIP1 | NM_001002233, NM_001002814, NM_025151 |
| RALGDS | NM_006266 |
| RFC4 | NM_002916, NM_181573 |
| RNF2 | NM_007212 |
| RPL27 | NM_000988 |
| RRM1 | NM_001033 |
| RRM2 | NM_001034 |
| RTKN | NM_001015055, NM_001015056, NM_033046 |
| SCARA3 | NM_016240, NM_182826 |
| SCUBE2 | NM_020974 |
| SEC61A1 | NM_013336 |
| SERF1A | NM_021967 |
| SIAH2 | NM_005067 |
| SLC2A3 | NM_006931 |
| SLC7A10 | NM_019849 |
| SLC28A1 | NM_004213, NM_201651 |
| SLC28A2 | NM_004212 |
| SLC29A1 | NM_004955 |
| SLC29A2 | NM_001532 |
| SLC35B1 | NM_005827 |
| SM20 | NM_022051 |
| SOD1 | NM_000454 |
| SPARC | NM_003118 |
| STK15 | NM_003600, NM_198433, NM_198434, NM_198435, NM_198436, NM_198437 |
| STOML1 | NM_004809 |
| SURF4 | NM_033161 |
| SURVIVIN | NM_001012270, NM_001012271, NM_001168 |
| TBPL1 | NM_004865 |
| TCEB3 | NM_003198 |
| TDP1 | NM_001008744, NM_018319 |
| TFRC | NM_003234 |
| TGFB3 | NM_003239 |
| TIMP1 | NM_003254 |
| TIMP3 | NM_000362 |
| TLOC1 | NM_003262 |
| TNC | NM_002160 |
| TNF | NM_000594 |
| TNFSF6 | NM_000639 |
| TOP1 | NM_003286 |
| TOP2A | NM_001067 |
| TP53 | NM_000546 |
| TRAG3 | NM_004909 |
| TUBB/TUBA2 | NM_178014, NM_006001, NM_079836 |
| TWIST | NM_000474 |
| TXN | NM_003329 |
| TYMS | NM_001071 |
| UBE2M | NM_003969 |
| UBCH10 | NM_007019, NM_181799, NM_181800, NM_181801, NM_181802, NM_181803 |
| UBPH | NM_019116 |
| UCH37 | NM_015984 |
| UMP-CMPK | NM_016308 |
| UMPS | NM_000373 |
| UP | NM_003364, NM_181597 |
| UPB1 | NM_016327 |
| USP22 | XM_042698 XP_042698 |
| WISP1 | NM_003882, NM_080838 |
| XIAP | NM_001167 |
| XIST | NR_001564 |
| XPA | NM_000380 |
| XPB | NM_000122 |
| XRCC1 | NM_006297 |

Analysis of the expression of one or more of the molecular predictors of response includes analysis of at least one gene in at least one pathway whose expression is activated to a higher or lower level in a patient suffering from a cancer relative to the expression in a normal or control subject. A differentially expressed gene may be activated or inhibited at the nucleic acid level or protein level, or may be subject to alternative splicing to result in a different polypeptide product. Such differences may be evidence by a change in RNA levels, surface expression; secretion or other cellular polypeptide expression patterns. Differential gene expression may include a comparison of the ratios of the expression between two or more genes or their gene products or a comparison of two differently processed products of the same gene which differ between normal subjects and subjects suffering from a cancer. Differential expression includes quantitative and qualitative differences in the temporal or cellular expression patterns in a gene or its expression product among normal and tumor cells.

Any one or more of the methods, assays, tools, systems or any subpart of any method, assay, tool or system, disclosed herein may be used alone, combined with, or used optionally with, any other method, assay, tool or system, or subpart of any method, assay, tool or system, disclosed herein. As a non-limiting example, the cell culture protocol of Sections II and III, or any subsection thereof (for example, III(a)-III(e)), may optionally be used together with any one or more of Sections IV (Combination Treatment), Section V (Preparation and Determination of Dose Levels), Section VI (Determination of Phenotypic and Genotypic Drift), Section VII (Methods of Generating Dose Response Curves), Section VIII (Methods of Cell Fixing and Staining), Section IX (Targeting Agents), Section X (Pharmaceutical Agents), Section XI (Apoptosis Assay), Section XII (Choice of Agents) and Section XIII (Molecular Predictors of Response). As another non-limiting example, the cells obtained from the cell culture protocol of Sections II and III, or any subsection thereof, may optionally be used in the methods of one or more of Sections IV (Combination Treatment), Section V (Preparation and Determination of Dose Levels), Section VI (Determination of Phenotypic and Genotypic Drift), Section VII (Methods of Generating Dose Response Curves), Section VIII (Methods of Cell Fixing and Staining), Section IX (Targeting Agents), Section X (Pharmaceutical Agents) and Section XI (Apoptosis Assay). In another non-limiting example, the cells obtained from the culture protocols of Sections II and III may be treated as in Section IV (Combination Treatment) or the cells may be examined as in Section VI for determination of phenotypic and/or genotypic drift and optionally used as in Section XI, the apoptosis assay. As stated above, cells from any of the foregoing methods may be assayed with respect to changes in one or more molecular predictors of response.

In addition, any one or more of the assays, methods, tools or systems disclosed herein may optionally be substituted by one or more assays, methods, tools or systems known in the art and publicly available. As a non-limiting example, the cells generated from the protocol of Sections II and/or III may be contacted by any stain or molecule known in the art and visualized, and/or imaged and/or counted using any means for visualization and/or imaging and/or counting of cells known in the art.

The foregoing examples and limitations related therewith are intended to be illustrative and not exclusive. The practice of the methods included in the invention disclosed herein use, unless otherwise indicated, conventional techniques in molecular biology (including recombinant techniques), microbiology, cell biology, and biochemistry which are within the skill in the art. Such techniques are explained fully in the literature, such as "Molecular Cloning: A Laboratory Manual," 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" 4th edition (D. M. Weir & C. C. Blackwell, eds., Blackwell Science, Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and, "PCR: The Polymerase Chain Reaction," (Mullis et al., eds., 1994). See, for example, WO 2004/065583.

EXAMPLES

Example 1

Initiation of a Primary Culture

A tumor biopsy of approximately 100 mg of non-necrotic, non-contaminated tissue was harvested from a patient by surgical biopsy and transferred to the laboratory in a standard shipping container. Biopsy sample preparation proceeded as follows. Reagent grade ethanol was used to wipe down the surface of a Laminar flow hood. The tumor was then removed, under sterile conditions, from its shipping container and was systematically minced by using two sterile scalpels in a scissor-like motion. The tumor particulates each measured about 1 mm$^3$. After each tumor quarter was minced, the particles, either agitated or non-agitated, were plated in culture flasks using sterile pasteur pipettes (approximately 9 explants per T-25 or approximately 20 particulates per T-75 flask). Each flask was then labeled with the patient's code, the date of explanation and any other distinguishing data. The explants were evenly distributed across the bottom surface of the flask, with initial inverted incubation in a humidified 37° C. incubator for 5-10 minutes, followed by addition of about 5-10 ml sterile growth medium and further incubation in the normal, non-inverted position. Flasks were placed in a humidified 37° C., 5% $CO_2$ incubator. Flasks were checked daily for growth and contamination. Over a period of a few weeks, with weekly removal and replacement of appropriate volume of growth medium, the explants grew out into a monolayer.

Example 2

Establishment of Concentrations for Each Dose

A multiple step drug dilution procedure that included 384 well microtiter plates and four ATCC cell lines to establish proper dose ranges to obtain cell killing from 0% up to and including maximal cell kill was used. Drugs were diluted in medium specific for each cell line and serial dilutions were made to provide ten drug concentrations. Drug dosages from step 1 were then validated on at least twenty patient-derived cell lines isolated from each of four major tumor types: ovarian, breast, lung and colon. Dosages were adjusted both on the low and the high end to get 0% up to and including maximal cell killing. Finally the newly determined dosages were further validated on patient cells using 384 well microplates and were further adjusted to get the whole spectrum of possible responses, from 0% up to and including maximal cell killing. Following the establishment of 72 hour dosing levels for several of the drugs that we test as single agents, a new method of dealing with combination treatments was developed.

Example 3

Combination Treatment

Separate 50 mg samples from residual tissue from specimens from four human ovarian tumors were minced in medium with sterile scissors to a particle size of roughly 1 mm$^3$ and with a particle size distribution between about 0.25 and about 1.5 mm$^3$. The minced samples were placed into at least one, possible multiple, tissue culture flasks with complete medium, and visual confirmation was made that the particulates were evenly distributed along the bottom of each flask and the flasks were placed in a 37° C., 5% $CO_2$ incubator. Flasks were checked daily for growth and contamination. Over a period of a few weeks, with weekly removal and replacement of growth medium, the particulates grew into monolayers.

Enough cells were then removed from the monolayers grown in the flasks for centrifugation into standard size cell pellets for each flask. Each cell pellet was then suspended in 5 ml of the above-described medium and was mixed in a conical tube with a vortex for 6 to 10 seconds, followed by manual rocking back and forth 10 times. A 30 µl droplet from the center of each tube was then pipetted into one well of a 96-well microtiter plate together with an equal amount of trypan blue, plus stirring. The resulting admixture was placed on each side of a hemocytometer for examination using a standard light microscope. Cells were counted in five out of nine hemocytometer quadrants on each side, under 10× magnification—only those cells which had not taken up the trypan blue dye were counted. An average cell count per chamber was calculated and by means known in the art the optimum concentration of cells in the medium was determined.

Accommodating the above calculations, additional cell aliquots from the other culture flasks were separately suspended in growth medium via vortex and rocking and then were loaded into separate channels of an 8-channel deep well plate. Aliquots of the prepared cell suspension were delivered into the 384 well microtiter plates using an automated liquid handler with techniques known in the art. Cells were plated into each well of the microtiter plates at a concentration of 320 cells per well.

Approximately twenty-four (24) hours post-plating, the chemotherapeutic agents paclitaxel and carboplatin were applied to the wells in the microtiter plates in increasing dosages. The first columns of the plate served as control wells with no treatment. The tumor cells in the wells were then incubated with the chemotherapeutic drugs for another 72 hours.

Fraction surviving treatment calculated as the cell number relative to control. For the cells from the tumor specimens a dose response relationship was observed for paclitaxel/carboplatin treatment schema.

Example 4

Digestion of Ovarian Tumor Specimen and Preparation of a Cell Culture Monolayer

Ovarian tumor tissue was received and minced into pieces approximately 5 $mm^3$. Each cut specimen was placed in a 15 ml conical tube containing 10 ml of 0.25% Collagenase II and 0.001% DNase I in Hank's Balanced Salt Solution (HBSS) with $Ca^{2+}$ and $Mg^{2+}$. Specimens were then incubated for about 15 to 30 minutes in a 37° C. incubator on a rocking platform.

After the thirty minute incubation, specimens were centrifuged for 3 minutes at 2200 RPM. The sample media (HBSS with $Ca^{2+}$ and $Mg^{2+}$) was poured off of the specimens, and specimens were rinsed with 10 ml of 10% McCoy's media. Samples were centrifuged again for 3 minutes at 2200 RPM, followed by removal of sample media. After pouring off the sample media, samples were centrifuged again to remove media and residual Collagenase II and DNase from the cells.

Each sample was then placed in a non-vitrogen coated flask in 10% McCoy's media and placed in a 37° C. incubator. The media was changed as necessary (twice a week or more) depending on the growth of cells. Once the cells began to grow, the media changes involved a rinse step to remove residual Collagenase II and DNase I.

Example 5

Assays of the Chemoresistant Cell Population

In one embodiment of the methods disclosed herein, tumor cells determined to be chemoresistant by the methods disclosed herein may be cultured according to ChemoFx® Assay V1 or V2 protocols. The chemoresistant cells obtained by the methods disclosed herein may be used in, or with, any of the other methods, assays, tools or systems disclosed herein, or with any methods, assays, tools or systems known in the art. Tumor cells determined to be chemoresistant by other methods known in the art may also be cultured according to ChemoFx® Assay V1 or V2 protocols disclosed herein. In either instance, additional chemosensitivity testing and/or genotypic and/or phenotypic and/or apoptotic assays and/or evaluation of one or more molecular predictors of response will be subsequently performed on the cultured chemoresistant tumor cells.

For example, and not by way of limitation, according to Version 1 of the ChemoFx® Assay, chemoresistant cells can be seeded into 60 well microtiter plates at a density of about 100-150 cells per well and allowed to attach and grow for about 24 hours. After about 24 hours in culture the cells can be exposed for about 2 hours to a battery of chemotherapeutic agents. At the end of the incubation with the chemotherapeutic agents, the plates will be washed to remove non-adherent cells. The remaining cells can be fixed with 95% ethanol and stained with the DNA intercalating blue fluorescent dye, DAPI, or 6-diamidino 2-phylindole dihydrochloride (Molecular Probes, Eugene, Oreg., USA). The surviving cells are then counted using an operator-controlled, computer-assisted image analysis system (Zeiss Axiovision, Thornwood, N.Y., USA). A cytotoxic index can be calculated using methods known in the art. The data can be presented graphically as the Cytotoxicity Index (CI). A dose-response curve can be generated for each drug evaluated.

In another nonlimiting example, according to Version 2 of the ChemoFx® Assay, a cell suspension of primary tumor cells can be prepared at a concentration of about 8,000 cells/ml and delivered in a large basin to the stage of a liquid handling machine. The machine then seeds about 320 cells in 40 µl of medium into the wells of a 384 well microplate in replicates of 4, after which the cells are allowed to adhere to the plate and grow for about 24 hours at 37° C. Following the 24 hour incubation, the liquid handling machine prepares ten doses of each drug, in the appropriate growth medium, via serial dilutions in a 96 well deep-well microplate. When the drugs are ready, the liquid handling machine dispenses 40 µl of 2× drug into the appropriate wells of the deep well plate. Proprietary software, named Resource Allocator, ensures that the cells are treated with the correct drugs and dosages. Resource Allocator determines the settings and layout for the liquid handler based on the number of patient specimens that are ready for processing (achieved required confluence in the culture flasks) and the number of drugs required for each patient specimen. After processing the information, Resource Allocator provides a script to the operator indicating where each plate, basin, and deepwell plate must be put. Subsequently to configuring the liquid handler, the operator initiates the Resource Allocator software to plate cells or dilute drug or treat specimens. After treatment, the drugs are left on the cells for about a 72 hour incubation, thus necessitating their preparation in growth medium. During this period, cell viability can be maintained in a standard tissue culture incubator, and visible, UV or fluorescent light images are taken at predetermined intervals using proprietary software.

At the end of the 72 hour incubation period, the liquid handling machine is used to remove the media and any non-adherent cells. Then, the remaining cells will be fixed 5 minutes in 95% ethanol containing the DNA intercalating blue fluorescent dye, DAPI. Following fixation and staining, the automated microscope can be used to take UV images of the stained cells in every well. Afterwards, the number of cells per well in both visible and UV light can be quantified using proprietary software named Cell Counter. Cell Counter identifies cells from the background of images mathematically manipulating the images to increase contrast. Subsequent processing uses the threshold based on the pixel histogram of the image to determine the number of cells within the image.

A complete dose response curve can be generated for each drug evaluated by comparing cells remaining at each dose to the untreated control wells. An image analysis system is used in analysis of the cells. Here, chemoresistant cells grown in plates are imaged on a Nikon TE300 Eclipse inverted microscope equipped with a motorized stage and a Photometrics Cool Snap FX CCD camera.

In one embodiment of this invention, the non-adherent cells are collected from the microtiter plate for subsequent analysis. Such analysis could include genotypic or phenotypic measurements, such as cell viability, genetic stability analysis, ability to form secondary cultures either in a ChemoFx assay Version 1 or version 2, or other analysis of someone skilled in the art.

In one embodiment of the invention, the adherent, chemoresistant cells are analyzed prior to fixation and staining. Such analysis may include but is not limited to treating the remaining adherent cells with additional drugs to determine response to a second regiment of chemotherapeutic agents. Such analysis may include but is not limited to analysis of different vital stains to measure cell viability, membrane integrity, cell signaling pathways, apoptosis, multi-drug resistance (MDR) ability, etcetera. Such analysis may include but is not limited to genotypic analysis for gene expression or genome mutations, phenotypic analysis, such as expression of surface proteins, cell viability, immunohistochemical analysis and pathological analysis. Subsequence to analysis of adherent cells as mentioned above, the cells are fixed and stained for counting/analysis as described in Version 2 assay methodology.

Modification of ChemoFx® assays Versions 1 and Versions 2 disclosed herein are within the ordinary skill in the art. Inclusion of other assays, methods, procedures, tools, materials, drugs, systems, compounds and equipment known in the art is intended to be an option in the practice of the assays, methods, tools and systems included in the invention disclosed herein.

Chemoresistant cells may be cultured and subcultured repeatedly using one or more methods of the invention in order to determine an effective amount of an agent or combination of agents to provide a desired chemoresponse.

Example 6

Digestion of Colon Tumor Specimen and Preparation of a Cell Culture Monolayer

Colon tumor tissue (in shipping medium) was received and gently shaken three to four times. Shipping medium was poured off of the tumor and transferred to a 50 ml conical tube which was centrifuged for 3 minutes at 800×g. After centrifugation, the supernatant was poured off the resulting pellet. The tube containing the pellet were set aside for later use.

The solid tumor was transferred to an open, sterile Petri dish using sterile forceps as needed. Disposable sterile scalpels were used to mince the tumor into smaller explants to a size equivalent to one capable of being sucked up by a 10 ml pipette. Using 5 ml of antibiotic wash, small explants and floating cells were aspirated with a pipette and transferred to the tube containing the pellet.

The remaining larger explants were minced further to the size equivalent to one capable of being sucked up by a 5 ml pipette. Depending on the size of the colon tumor explant, 5 or 10 ml of antibiotic wash containing 1 or 2 ml of cocktail of 0.025% Collagenase II and 0.001% DNase was added to each sample. The antibiotic wash is Hanks solution containing penicillin, streptomycin, gentamicin, nystatin and ciprofloxacin. Explants were aspirated and transferred to a 15 ml conical tube. Once in the 15 ml tube, the explants were pipetted in and out to disaggregate the big explants. The tube was capped and shaken 2-3 times and then incubated for 15 minutes on a rocker in a 37° C. and 5% $CO_2$ incubator.

Both the conical tube containing the small explants and the tube which had contained the larger explants were centrifuged for three minutes at 800×g. After centrifugation, supernatants were removed from the resulting pellets. The pellet resulting from the smaller explants was resuspended in 3 ml of RPMI-1640 cell culture medium containing 2% FBS and antibiotics and transferred to a labeled T-25 flask. The pellet resulting from the larger explants (the explants treated with Collagenase II and DNase) were treated with 3 ml or 6 ml of RPMI-1640 containing 2% FBS (depending on the size of the pellet) and transferred to a labeled T-25 or T-75 flask.

Both flasks were swirled evenly to distribute the explants. Flasks were propped on an angle in the hood for ten minutes to allow as much media but as few explants as possible drain to the bottom edge of the flask.

The explants were transferred to new flasks such that 30-50% of the bottom of the flask(s) was covered with explants. The flasks containing the explants were incubated at 37° C. and 5% $CO_2$ to allow for cell growth. Cell media was changed as needed.

Example 7

Determination of Normalized Cytotoxicity Index

Cytotoxicity Index scores were normalized to account for variations in the starting number of cells assayed. Twenty-four hours after cells were placed in wells, i.e., segregated sites, plates were removed from the incubator and placed on an imaging system. Each well of the plate was imaged by the imaging system to capture visible and fluorescent images. Each image was analyzed and the number of cells in each well was determined.

Cells were then treated with an agent. Untreated cells were used as a control. At the completion of the assay, cells were counted again. The Cytotoxicity Index (CI) was calculated using cell counts pre-treatment and post-treatment (test and control groups) as follows:

$$CI = \frac{T_{end\ treated} \times T_{24\ untreated}}{T_{end\ untreated}\ T_{24\ treated}}$$

wherein $T_{end}$ is the post-treatment cell count and $T_{24}$ is the pre-treatment cell count.

All cited patent, patent applications, publications and documents mentioned in the above specification are herein incorporated by reference in their entirety. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of cell biology, and/or related fields are intended to be within the scope of the following claims.

We claim:

1. A method for testing sensitivity of a tumor to a chemotherapeutic agent or combination, comprising:
    mincing an epithelial tumor specimen to prepare a plurality of multicellular tissue explants, and placing the explants in liquid medium in one or more containers;
    physically agitating the explants, culturing said explants to form one or more non-confluent monolayers, and suspending the non-confluent monolayer(s) in culture medium to obtain from about 4,000 to about 12,000 cells per ml;
    transferring the cells to a plurality of wells at about 100 to about 1000 cells per well;
    adding a serial dilution of at least one chemotherapeutic agent or combination across the wells; and
    determining sensitivity of the cells to the chemotherapeutic agent or combination.

2. The method of claim 1, wherein the explants are physically agitated by swirling, shaking, or rocking the container, or striking the container against a solid object.

3. The method of claim 1, wherein the cells are incubated in the plurality of wells for about 4 to 30 hours before the chemotherapeutic agent or combination is added.

4. The method of claim 1, wherein chemosensitivity is determined by quantifying cell death.

5. The method of claim 4, further comprising, preparing a dose response curve.

6. The method of claim 1, wherein the tumor is a breast, colorectal, or ovarian tumor.

7. The method of claim 1, wherein the epithelial tumor specimen contains from 15 to 35 mg of tissue.

8. The method of claim 1, wherein the explants each measure from 0.25 mm$^3$ to 1.5 mm$^3$.

9. The method of claim 1, wherein the explants are treated with one or more of Collagenase and DNase.

10. The method of claim 1, wherein the tumor specimen is an ovarian or colorectal tumor specimen, and the explants are treated with one or more of Collagenase and DNase.

11. The method of claim 1, wherein the explants are removed from culture when the monolayer is at about 10% to about 50% confluency.

12. The method of claim 1, further comprising monitoring the morphology and/or growth rate of the monolayer cells.

13. The method of claim 12, wherein the monolayer cells are monitored by phase contrast microscopy.

14. The method of claim 1, wherein the cells are suspended at about 8,000 cells/ml.

15. The method of claim 1, wherein about 200 to 400 cells are seeded per well.

16. The method of claim 15, wherein the cells are incubated in the wells for about 24 hours prior to contact with the chemotherapeutic agent or combination.

17. The method of claim 1, wherein the cells are contacted with the chemotherapeutic agent or combination for about 25 to 200 hours.

18. The method of claim 1, wherein cell death is quantified by fixing and staining the cells, and visualizing stained cells.

19. A method for testing sensitivity of a tumor to a chemotherapeutic agent or combination, comprising:
    disaggregating an ovarian or colorectal tumor specimen to prepare a plurality of explants;
    treating the explants with DNase and Collagenase while disturbing the explants with a swirling, shaking, or rocking motion so as to reduce the size of the explants, wherein the treated explants are multicellular tissue explants;
    culturing the multicellular tissue explants to form one or more non-confluent monolayers comprising malignant cells;
    suspending the non-confluent monolayer(s) in culture medium at about 4,000 to 12,000 cells per ml, and transferring the cells to a plurality of wells at about 100 to 1000 cells per well;
    incubating the cells for about 4 to 30 hours, and then adding a serial dilution of the chemotherapeutic agent or combination across the wells;
    quantifying cell death in each well as a measure of chemosensitivity, and
    preparing a dose response curve for the chemotherapeutic agent or combination.

20. The method of claim 19, wherein the explants are treated with a DNase and Collagenase II cocktail for from 3 minutes to one hour, the cocktail comprising from about 0.01% to about 0.6% of Collagenase II and from about 0.0007% to about 0.005% of DNase.

21. The method of claim 20, wherein the explants are removed from culture when the monolayer is at about 10% to about 50% confluency.

* * * * *